United States Patent
Kobayashi et al.

(10) Patent No.: US 6,228,547 B1
(45) Date of Patent: May 8, 2001

(54) BIS(3,4-METHYLENEDIOXYPHENYLAMINO) DERIVATIVES AND ELECTROPHOTOGRAPHIC PHOTORECEPTOR CONTAINING THE DERIVATIVES

(75) Inventors: Tohru Kobayashi; Yoshimasa Matsushima; Yoko Aoki; Mamoru Yamada; Hiroshi Sugiyama; Toshimitsu Hagiwara, all of Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/332,940

(22) Filed: Jun. 15, 1999

(30) Foreign Application Priority Data

Jun. 16, 1998 (JP) .................................................. 10-183294

(51) Int. Cl.⁷ ............................ G03G 5/06; C07D 317/48
(52) U.S. Cl. ...................... 430/72; 430/58.75; 430/58.85; 430/59.4; 430/73; 430/75; 430/83; 549/435
(58) Field of Search ................................. 430/56, 58.75, 430/58.8, 59.4, 75, 73, 72, 83; 549/434, 435

(56) References Cited

U.S. PATENT DOCUMENTS

| | | |
|---|---|---|
| 3,265,496 | 8/1966 | Fox . |
| 4,265,990 * | 5/1981 | Stolka et al. ............... 430/96 |
| 5,312,707 * | 5/1994 | Ota et al. .................. 430/83 |
| 5,334,470 | 8/1994 | Shimada et al. ............ 430/83 |
| 5,378,569 * | 1/1995 | Nukada et al. ............. 430/58.8 |
| 5,399,453 | 3/1995 | Dohi et al. ................ 430/72 |
| 5,436,100 | 7/1995 | Shimada et al. ............ 430/71 |
| 5,475,137 | 12/1995 | Shimada et al. ............ 564/308 |
| 5,494,766 | 2/1996 | Dohi et al. ................ 430/83 |
| 5,804,344 * | 9/1998 | Mitsumori ................. 430/73 |

FOREIGN PATENT DOCUMENTS

| | | |
|---|---|---|
| 1-142641 * | 6/1989 | (JP) . |
| 6-342215 | 12/1994 | (JP) . |
| 7-225486 | 8/1995 | (JP) . |

OTHER PUBLICATIONS

Derwent Abstract Acc. No. 1989–203379 (Jun. 1989), Which Describes Japanese Patent 1–142641.*

* cited by examiner

Primary Examiner—Janis L. Dote
(74) Attorney, Agent, or Firm—Sughrue, Mion, Zinn, Macpeak & Seas, PLLC

(57) ABSTRACT

Disclosed are novel compounds useful in electrophotographic photoreceptors as charge-transporting materials having good miscibility with binder polymers and capable of forming a thin stable organic film having a high concentration; and an electrophotographic photoreceptor containing the same. The compounds are bis(3,4-methylenedioxyphenylamino) derivatives represented by general formula (1):

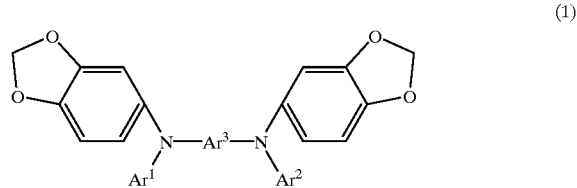

(1)

wherein $Ar^1$ and $Ar^2$ each is an optionally substituted aryl group and $Ar^3$ is a phenylene group or an optionally substituted biphenylene group.

6 Claims, 2 Drawing Sheets

BIS(3,4-METHYLENEDIOXYPHENYLAMINO) DERIVATIVES AND ELECTROPHOTOGRAPHIC PHOTORECEPTOR CONTAINING THE DERIVATIVES

FIELD OF THE INVENTION

The present invention relates to novel bis(3,4-methylenedioxyphenylamino) derivatives represented by the following general formula (1) and an electrophotographic photoreceptor containing one or more of the derivatives:

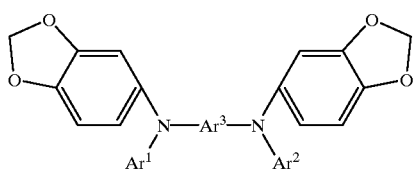

(1)

wherein $Ar^1$ and $Ar^2$ may be the same or different and each represents an optionally substituted aryl group; and $Ar^3$ represents a divalent aromatic group represented by

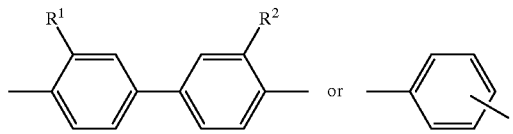

wherein $R^1$ and $R^2$ each represents a hydrogen atom, an alkyl group having 1 to 4 carbon atoms, or a phenyl group, provided that when $Ar^3$ is a phenylene group, one of the amino substituents is meta or para to the other.

BACKGROUND OF THE INVENTION

Recently, printers as terminal recording apparatuses in the field of information communications are being strongly required more and more to be of smaller size and capable of higher-rate printing and color printing. Because of this, electrophotographic photoreceptors for use in electrophotographic laser beam printers or LED printers have come to be required to be of even smaller size and capable of coping with a higher printing rate.

In order to obtain such an excellent electrophotographic photoreceptor, it is, of course, necessary to employ a charge-generating substance and a charge-transporting substance each having satisfactory properties. Besides this, it is also important that the injection of charge carriers from the charge-generating substance into the charge-transporting substance, i.e., the injection of charges from a charge-generating layer into a charge-transporting layer, should be efficiently conducted. Since this charge injection depends on the properties of the interface between the charge-generating substance (or charge-generating layer) and the charge-transporting substance (or charge-transporting layer) and varies with combinations of various substances, charge-transporting substances having a variety of properties are being developed.

N,N'-Diphenyl-N,N'-bis(3-methylphenyl)-4,4'-biphenylenediamine (4) is already known to effectively function as a charge-transporting material (see JP-B-58-32372 (the term "JP-B" as used herein means an "examined Japanese patent publication") and U.S. Pat. No. 3,265,496).

Several diaminobiphenyl compounds also are known as charge-transporting materials (see JP-B-63-6864, JP-B-5-40904, Japanese Patent 2,539,641, EP 0648737 A1, JP-A-6-199745 (the term "JP-A" as used herein means an "unexamined published Japanese patent application"), JP-A-6-293716, JP-A-7-188130, JP-A-7-181693, and U.S. Pat. No. 5,399,453).

Electrophotographic photoreceptors are known which employ a mixture of a diaminobiphenyl compound having two or more alkoxy groups on the same aromatic ring and other charge-transporting material(s) (see JP-A-7-225486, JP-A-6-342215, JP-A-6-342220, JP-A-6-342218, JP-A-6-342217, JP-A-6-342216, JP-A-5-341545, and JP-A-5-341544).

Combinations of a diaminobiphenyl compound and a binder polymer are known (see JP-A-7-120941, JP-A-6-214412, and JP-A-6-130685).

Also known are combinations of a diaminobiphenyl compound and a charge-generating material (see JP-A-6-75408, JP-A-6-161132, JP-A-6-75403, JP-A-5-257310, JP-A-5-188615, JP-A-5-281769, and JP-A-5-257309).

Applications of m-diaminobenzene derivatives to materials for electrophotographic photoreceptors are described, e.g., in JP-A-1-142642 and JP-A-5-88389. An m-diaminobenzene derivative having a fluoroalkyl group bonded to the central benzene ring is described in JP-A-7-126224, and an electrophotographic photoreceptor employing this derivative is described in JP-A-1-128880. JP-A-3-105347 discloses an m-diaminobenzene derivative having a thiocarbonyl group. An m-diaminobenzene derivative having a methoxy group and a phenyl group bonded as substituents to the central phenyl group is described in JP-A-2-93653, and an electrophotographic photoreceptor employing this derivative is described in JP-A-2-93654. In JP-A-5-58966 and JP-A-5-301848 are disclosed m-diaminobenzene derivatives in which one of the amino groups is substituted with a pyrene ring. JP-A-4-300853 discloses a diaminobenzene derivative having an olefin substituent and an electrophotographic photoreceptor employing this derivative. Furthermore, an electrophotographic photoreceptor employing a diaminobenzene compound having three or four amino substituents in the molecule is disclosed in JP-A-3-94258 and JP-A-3-94259.

As described above, electrophotographic photoreceptors employing a compound selected from many diaminobiphenyl or diaminobenzene compounds have been proposed. However, these compounds have drawbacks that they are apt to separate out as crystals because of their insufficient solubility, have poor miscibility with binder polymers, and are insufficiently compatible with phthalocyanines suitable for use as charge-generating materials. Consequently, there have been cases where the prior art electrophotographic photoreceptors have insufficient photosensitivity or have a high residual potential to cause scumming.

SUMMARY OF THE INVENTION

An object of the present invention is to provide novel charge-transporting materials having a high carrier mobility and high sensitivity which have satisfactory miscibility with binder polymers, are capable of forming a thin stable organic film having a high concentration, and give an electrophotographic photoreceptor having various excellent properties.

Under the circumstances described above, the present inventors synthesized various compounds and made intensive investigations thereon in order to find out both a charge-transporting material having a high mobility and capable of giving a thin stable organic film even when used at a high concentration and a compound suitable for use in producing a high-performance electrophotographic photoreceptor. As a result, they have found that the problems described above can be eliminated with novel bis(3,4-methylenedioxyphenylamino) derivatives represented by the following general formula (1):

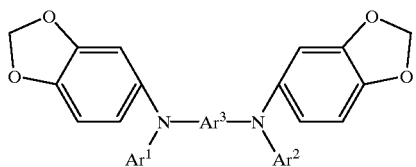

(1)

wherein $Ar^1$ and $Ar^2$ may be the same or different and each represents an optionally substituted aryl group; and $Ar^3$ represents a divalent aromatic group represented by

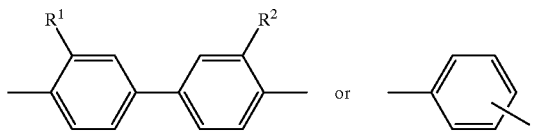

wherein $R^1$ and $R^2$ each represents a hydrogen atom, a lower alkyl group having 1 to 4 carbon atoms, or a phenyl group, provided that when $Ar^3$ is a phenylene group, one of the amino substituents is meta or para to the other. The present invention has been completed based on this finding.

The compounds represented by general formula (1), even when used in a high concentration, neither separate out as crystals nor develop pinholes. Photoreceptors employing any of these compounds have high sensitivity and a low residual potential.

The present invention include the following (1) to (5).

(1) Novel bis(3,4-methylenedioxyphenylamino) derivatives represented by general formula (1) described above.

(2) An electrophotographic photoreceptor containing as a charge-transporting material at least one member selected from the novel bis(3,4-methylenedioxyphenylamino) biphenyl derivatives and bis(3,4-methylenedioxyphenylamino)benzene derivatives represented by general formula (1).

(3) An electrophotographic photoreceptor comprising a charge-generating material and a charge-transporting material, wherein the charge-generating material comprises a phthalocyanine and the charge-transporting material comprises a combination of at least one member selected from the bis(3,4-methylenedioxyphenylamino)biphenyl derivatives and bis(3,4-methylenedioxyphenylamino)benzene derivatives represented by general formula (1) and at least one of diaminobiphenyl compounds represented by the following general formula (2):

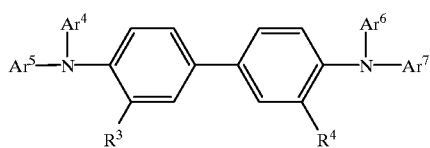

(2)

wherein $R^3$ and $R^4$ may be the same or different and each represents a hydrogen atom, a halogen atom, a lower alkyl group having 1 to 4 carbon atoms, a lower alkoxy group having 1 to 4 carbon atoms, or a phenyl group; and $Ar^4$, $Ar^5$, $Ar^6$, and $Ar^7$ may be the same or different and each represents a phenyl group which may have one or more substituents selected from the group consisting of halogen atoms, lower alkyl groups having 1 to 4 carbon atoms, and lower alkoxy groups having 1 to 4 carbon atoms or an α-naphthyl, β-naphthyl, or biphenyl group which may have one or more substituents.

(4) An electrophotographic photoreceptor comprising a charge-generating material and a charge-transporting material, wherein the charge-generating material comprises a phthalocyanine and the charge-transporting material comprises a combination of at least one compound represented by general formula (1) and at least one diaminobiphenyl compound represented by the following general formula (3):

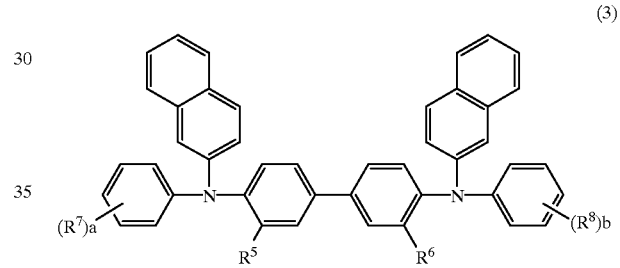

(3)

wherein $R^5$, $R^6$, $R^7$, and $R^8$ may be the same or different and each represents a hydrogen atom, a halogen atom, a lower alkyl group having 1 to 4 carbon atoms, a lower alkoxy group having 1 to 4 carbon atoms, or a phenyl group; and a and b each represents an integer of 1 or 2.

(5) An electrophotographic photoreceptor comprising a charge-generating material and a charge-transporting material, wherein the charge-generating material comprises a phthalocyanine and the charge-transporting material comprises a combination of at least one diaminobiphenyl compound represented by general formula (1) and the compound represented by the following formula (4).

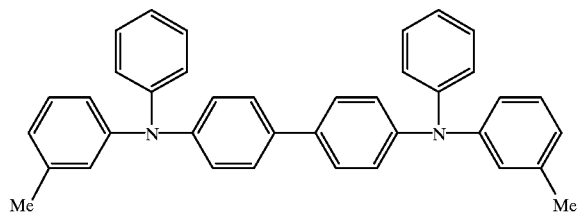

(4)

DETAILED DESCRIPTION OF THE INVENTION

Figure 1:
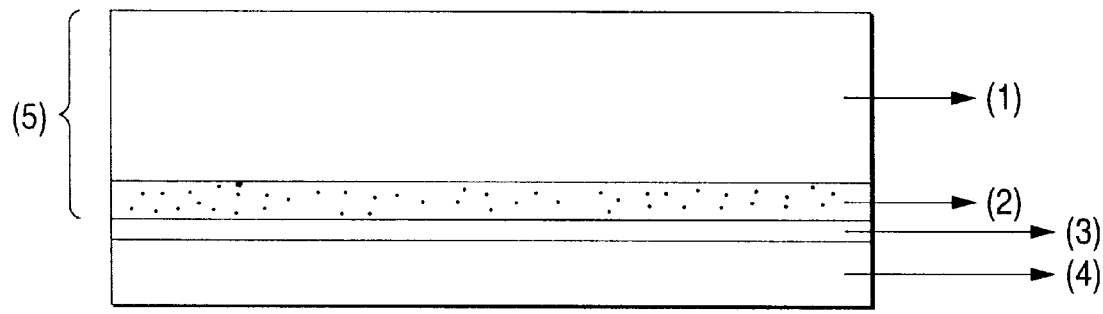
FIGS. 1(a)–(c) are views illustrating the constitutions of electrophotographic photoreceptors.
Figure 1:
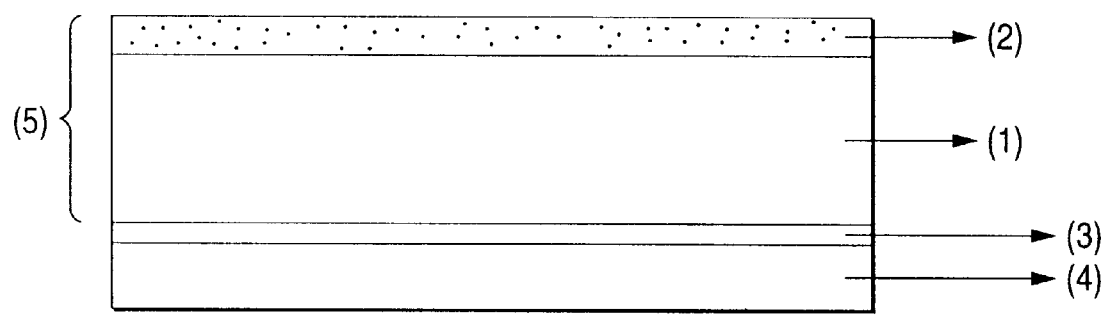
Figure 1:
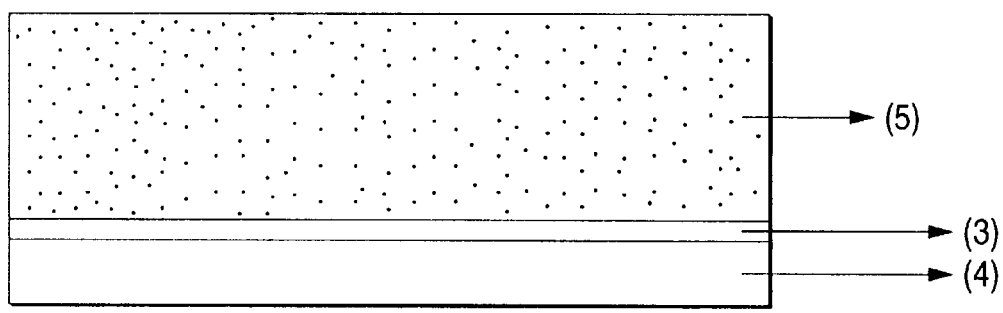

In the compounds represented by general formula (1) of the present invention, $Ar^1$ and $Ar^2$ may be the same or different and each represents an optionally substituted aryl group. Preferred examples thereof include a phenyl or naphthyl group which may be substituted with one or more lower alkyl groups having 1 to 4 carbon atoms.

Examples of the lower alkyl groups having 1 to 4 carbon atoms as the substituents of $Ar^1$ and $Ar^2$ include methyl, ethyl, propyl, n-butyl, isobutyl, and tert-butyl.

Especially preferred examples of the aryl group which may have such substituents include phenyl, p-tolyl, m-tolyl, p-ethylphenyl, 2,4-xylyl, and β-naphthyl.

Substituents $R^1$ and $R^2$ in $Ar^3$ in general formula (1) each represents a hydrogen atom, a lower alkyl group having 1 to 4 carbon atoms, or a phenyl group. Preferred are a hydrogen atom, methyl, and phenyl. More preferred are a hydrogen atom and methyl.

Preferred examples of the compounds represented by general formula (1) of the present invention include those given in the following Table 1. However, the compounds of the present invention should not be construed as being limited to these examples.

Exemplified Compound (1)

| No. | $Ar^1$ | $Ar^2$ | $Ar^3$ |
|---|---|---|---|
| 1 | phenyl | phenyl | 4,4'-biphenylene |
| 2 | p-tolyl (Me-) | p-tolyl (Me-) | 4,4'-biphenylene |
| 3 | m-tolyl (Me-) | m-tolyl (Me-) | 4,4'-biphenylene |
| 4 | 2,4-xylyl (Me-, Me-) | 2,4-xylyl (Me-, Me-) | 4,4'-biphenylene |
| 5 | p-ethylphenyl (Et-) | p-ethylphenyl (Et-) | 4,4'-biphenylene |
| 6 | β-naphthyl | β-naphthyl | 4,4'-biphenylene |
| 7 | α-naphthyl | α-naphthyl | 4,4'-biphenylene |

-continued
Exemplified Compound (1)
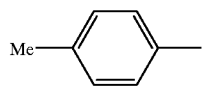
| No. | Ar¹ | Ar² | Ar³ |
|---|---|---|---|
| 8 | 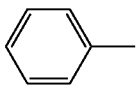 | 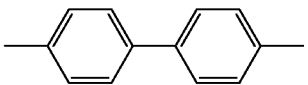 | 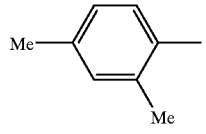 |
| 9 | 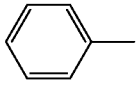 | 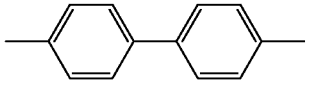 |  |
| 10 | 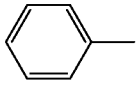 | 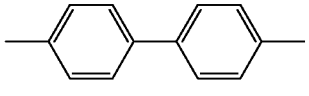 | 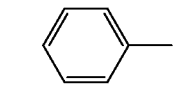 |
| 11 | 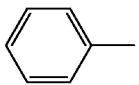 | 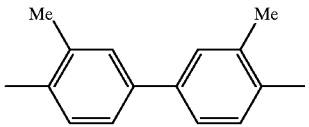 | 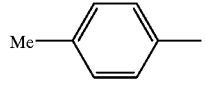 |
| 12 | 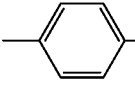 | 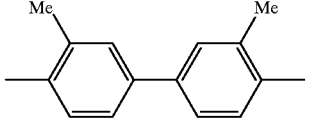 | 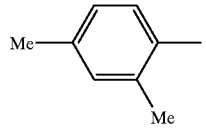 |
| 13 | 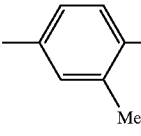 | 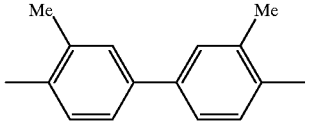 | 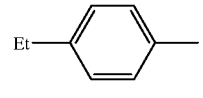 |
| 14 | 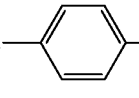 | 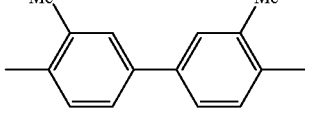 | 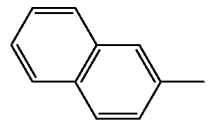 |
| 15 | 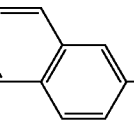 | 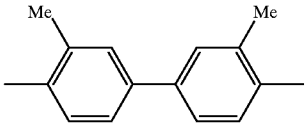 | 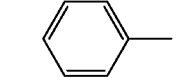 |
| 16 | 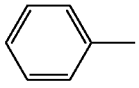 | 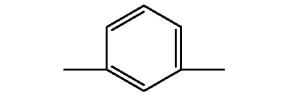 | |

-continued
Exemplified Compound (1)
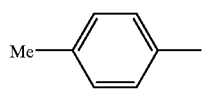
| No. | Ar¹ | Ar² | Ar³ |
|---|---|---|---|
| 17 | 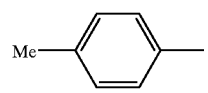 | 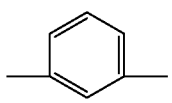 | 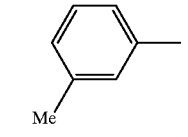 |
| 18 | 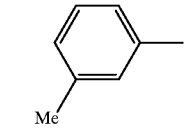 | 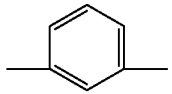 | 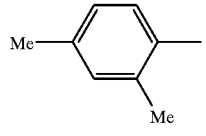 |
| 19 | 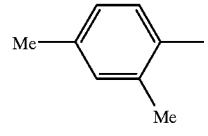 | 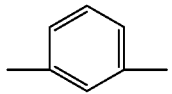 | 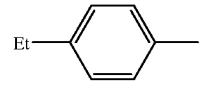 |
| 20 | 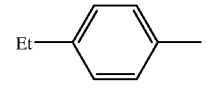 | 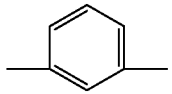 | 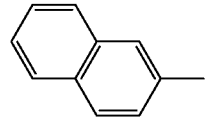 |
| 21 | 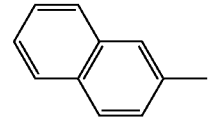 | 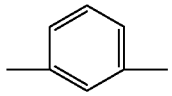 | 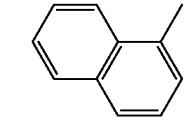 |
| 22 | 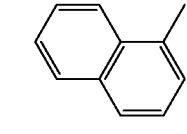 | 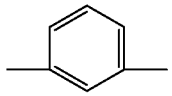 | 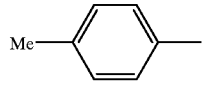 |
| 23 | 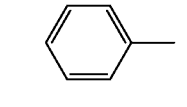 | 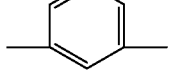 | 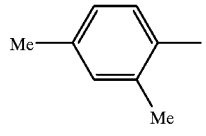 |
| 24 | 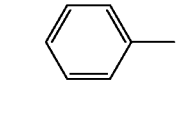 | 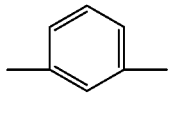 | 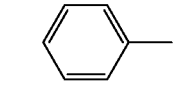 |
| 25 | 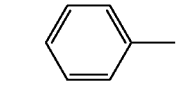 | 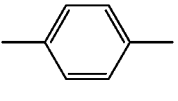 | 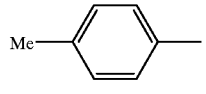 |
| 26 | 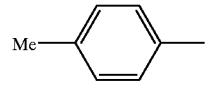 | 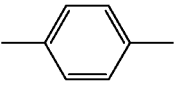 |  |

-continued

Exemplified Compound (1)

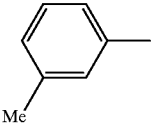

| No. | Ar¹ | Ar² | Ar³ |
|---|---|---|---|
| 27 | 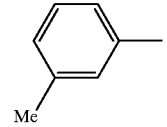 | 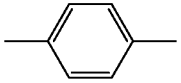 | 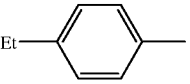 |
| 28 | 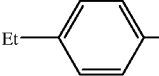 | 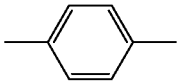 | 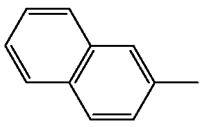 |
| 29 | 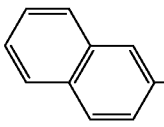 | 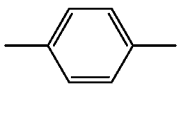 | 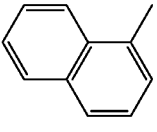 |
| 30 | 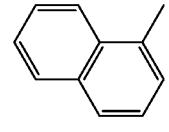 | 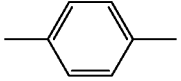 | |

Among the novel bis(3,4-methylenedioxyphenylamino) derivatives represented by general formula (1) of the present invention, the derivatives (1a) represented by general formula (1) wherein Ar¹=Ar² can be synthesized, for example, according to reaction formula 1.

Specifically, reactants consisting of 3,4-methylenedioxybromobenzene (5) and an aromatic acetamide (6) or of 3,4-methylenedioxyacetanilide (7) and an aromatic bromide (8) are subjected to the Ullmann reaction to obtain a coupling product (9). A copper powder or a copper salt such as a copper sulfate is used as a catalyst to conduct the above reaction in the presence of a base such as potassium carbonate or sodium carbonate. A solvent inert to the reaction, such as chlorobenzene, dichlorobenzene, nitrobenzene, diisopropylbenzene, or isobutylbenzene, is used for the reaction, which is preferably conducted at a temperature of from 170 to 230° C.

In some cases, a cyclic ether, e.g., a crown ether, or a linear ether also may be caused to be present in the reaction system.

Subsequently, the amide group of the coupling product (9) is decomposed with potassium hydroxide, sodium hydroxide, or the like in an alcohol solvent such as methanol or ethanol to convert the coupling product (9) into an amine (10). This reaction is preferably conducted at a temperature of about from room temperature to 80° C. The amine (10) is coupled with a dichloro-, dibromo-, or diiodo-substituted biphenyl or benzene (11), whereby a target compound (1a) of the present invention can be synthesized.

(Reaction formula 1)

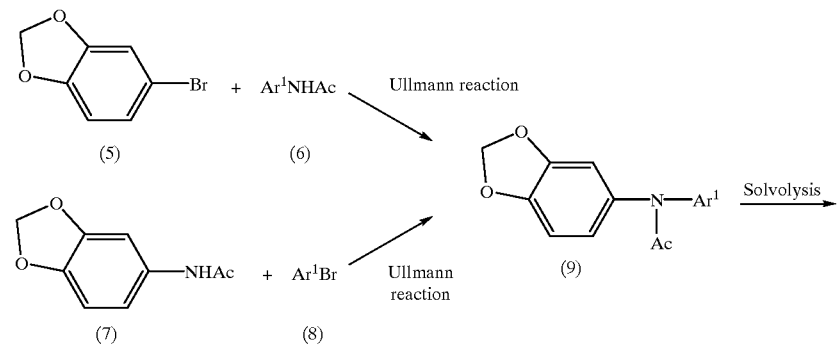

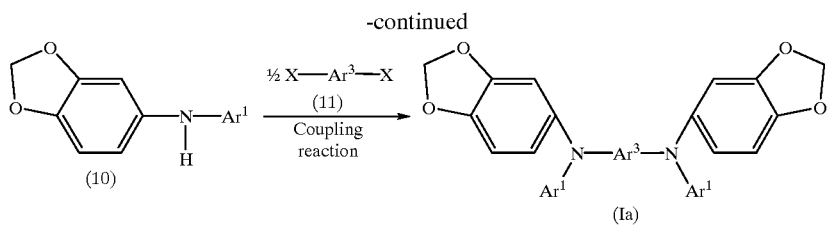

(In reaction formula 1, $Ar^1$ and $Ar^3$ have the same meanings as defined above, and X represents Cl, Br, or I.)

When the coupling reaction is conducted by the Ullmann reaction, the biphenyl or benzene derivative (11) is preferably a diiodide. This reaction can be carried out in the same manner as in the synthesis of the acetamide (9). When a transition metal complex catalyst is used for the coupling reaction, compound (11) may be any of dichloro, dibromo, and diiodo derivatives. Preferred examples of the transition metal complex catalyst include $Pd(dba)_2/2P(o\text{-tolyl})_3$ (dba: dibenzylideneacetone, o-tolyl: ortho-tolyl), $PdCl_2\{P(o\text{-tolyl})_3\}_2$, and a complex of palladium having a valence of 0 yielded by reacting a salt of palladium having a valence of 2 with a trialkylphosphine or triarylphosphine.

The amount of the complex catalyst may be about from 0.05 to 5% by mole based on the halogen as a substrate. The reaction may be conducted in a solvent inert to the reaction, such as, e.g., toluene, xylene, isobutylbenzene, or diisopropylbenzene, at a temperature of from 60 to 150° C. in the presence of an alkoxide such as, e.g., sodium tert-butoxide, potassium tert-butoxide, sodium methoxide, or sodium ethoxide. Thus, the target compound can be efficiently obtained.

Alternatively, the compounds of the invention represented by general formula (1a) can be synthesized according to reaction formula 2.

Specifically, 3,4-methylenedioxyacetanilide (7) and a dihalide (11) are subjected to the Ullmann coupling to synthesize a diacetamide derivative (12). This Ullmann reaction can be conducted under the same conditions as in the route shown by reaction formula 1. The solvolysis of compound (12) to compound (13) can be conducted in the same manner as the conversion of compound (9) to compound (10). If compound (12) has low solubility in alcohol solvents and the reaction thereof requires much time, then another solvent may be added such as, e.g., dimethyl sulfoxide (DMSO) or N,N-dimethylformamide (DMF). The diamine (13) thus obtained is coupled with an aromatic halide (14), whereby a target compound (1a) of the present invention can be synthesized. This coupling reaction may be conducted by either the Ullmann reaction or the reaction catalyzed by any of the aforementioned transition metal catalysts.

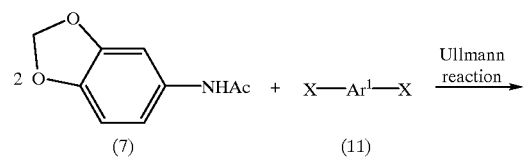

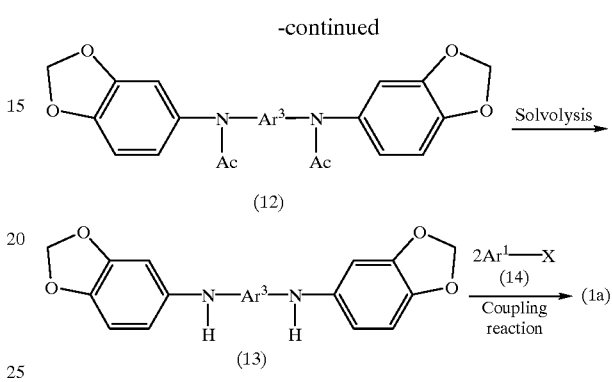

(In reaction formula 2, $Ar^1$ and $Ar^3$ have the same meanings as defined above, and X represents Cl, Br, or I.)

As shown in reaction formula 3, the diacetamide (12) can be synthesized also by subjecting a diacetyl compound (16) obtained from a diamine (15) and 3,4-methylenedioxybromobenzene (5) to the Ullmann coupling. It is also possible to directly convert the diamine (15) to compound (13) by the coupling reaction of the diamine (15) with 3,4-methylenedioxybromobenzene (5) in a molar ratio of 1:2 using any of the aforementioned transition metal complexes.

(Reaction formula 3)

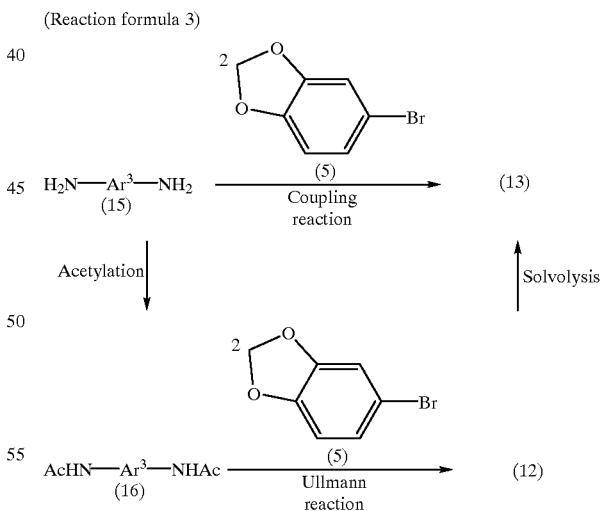

(In reaction formula 3, $Ar^3$ has the same meaning as defined above.)

Still another process usable for synthesizing a compound (1a) is illustrated by reaction formula 4. This process comprises subjecting a diamine (15) and an aryl halide (14) in a molar ratio of 1:2 to a coupling reaction using any of the aforementioned transition metal complexes to obtain a diamine (18) and then coupling the diamine (18) with 3,4-methylenedioxybromobenzene (5) in a molar ratio of 1:2. The diamine (18) can be synthesized also by subjecting a diacetyl compound (16) and an aryl halide (14) to the Ullmann reaction to obtain a compound (17) and solvolyzing the compound (17) with an alcohol.

(Reaction formula 4)

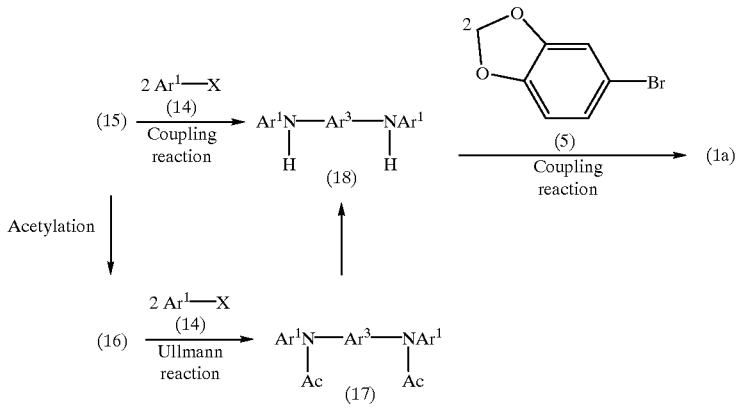

(In reaction formula 4, Ar¹ and Ar³ have the same meanings as defined above, and X represents Cl, Br, or I.)

Among the diaminobiphenyl derivatives or diaminobenzene derivatives represented by general formula (1) of the present invention, the bis(3,4-methylenedioxyphenylamino) derivatives (1b) represented by general formula (1) wherein Ar¹ ≠Ar² can be synthesized according to reaction formula 5.

Specifically, an amine (10) is coupled with an equivalent amount of a dihalide (11) to obtain a monoamino compound (19). This monoamino compound (19) is coupled with an amine (10') different from the amine (10) to thereby obtain an asymmetric bis(3,4-methylenedioxyphenylamino) derivative (1b). The two coupling reactions used here may be carried out in the same manner as those shown in reaction formulae 1 and 2.

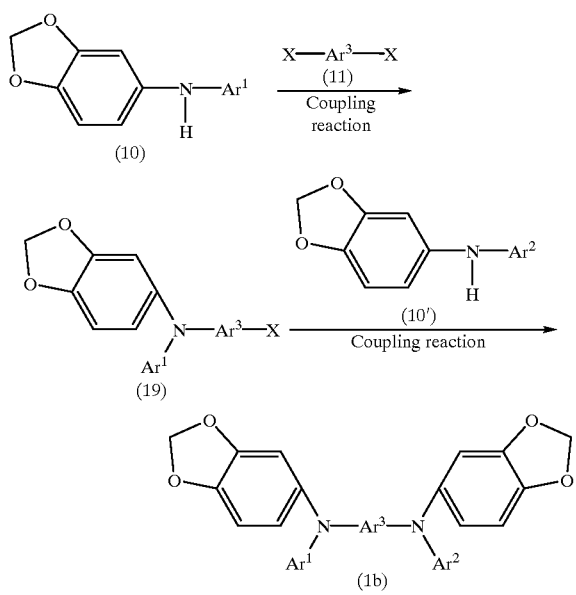

(In reaction formula 5, Ar¹ to Ar³ have the same meanings as defined above, and X represents Cl, Br, or I.)

The electrophotographic photoreceptor of the present invention contains any of the compounds represented by general formula (1) of the present invention, which are produced by the methods described above. An example of the electrophotographic photoreceptor is a lamination type electrophotographic photoreceptor comprising a conductive support and, formed thereon, a charge-generating layer and a charge-transporting layer which perform their respective functions. In this photoreceptor, the charge-transporting layer comprises a compound represented by general formula (1) of the present invention as a charge-transporting material.

As illustrated in FIG. 1, the above electrophotographic photoreceptor may have a structure in which the charge-transporting layer 1 is provided on the charge-generating layer 2 formed over the conductive support 4 (FIG. 1a) or a structure in which the charge-transporting layer 1 is provided under the charge-generating layer 2 (FIG. 1b). However, the charge-transporting layer 1 is desirably provided on the charge-generating layer 2. The use of the compounds represented by general formula (1) as charge-transporting materials is applicable also to a single-layer electrophotographic photoreceptor (FIG. 1c), in which a charge-generating material and one or more charge-transporting materials are contained in the same layer as a photosensitive layer 5.

The charge-transporting layer comprising a compound represented by general formula (1) of the present invention as a charge-transporting material is formed by vapor-depositing only the compound (1) as it is on a conductive support or on a charge-generating layer, or by dissolving the compound (1) of the invention in an appropriate solvent together with a binder, applying the solution on a conductive support or on a charge-generating layer, and drying the coating. On the other hand, the single-layer photoreceptor containing a charge generator and a compound (1) of the present invention is obtained by dissolving or dispersing the charge generator and the compound (1) of the invention in an appropriate solvent together with a binder, applying the solution on a conductive support, and drying the coating. A single-layer photoreceptor containing an electron acceptor compound and a compound (1) of the present invention can be obtained in the same manner as the above.

Examples of the binder include polycarbonates, polyesters, polystyrene, polyacrylates, polymethacrylates, polyamides, acrylic resins, vinyl chloride resins, vinyl acetate resins, epoxy resins, polyurethanes, and copolymers and mixtures thereof. Also usable besides such insulating polymers are organic photoconductive polymers such as polyvinylcarbazole, polyvinylanthracene, and polysilanes.

Especially preferred among these binders are polycarbonates. Examples of such preferred polycarbonates include bisphenol methane type polycarbonates represented by the following structural formula (A):

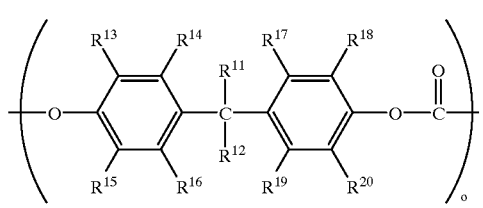
(A)

wherein $R^{11}$ and $R^{12}$ each independently represents a hydrogen atom, a lower alkyl group having 1 to 4 carbon atoms, a lower alkoxy group having 1 to 4 carbon atoms, or an optionally halogen-substituted phenyl group, provided that $R^{11}$ and $R^{12}$ may be bonded to each other to form a ring; $R^{13}$, $R^{14}$, $R^{15}$, $R^{16}$, $R^{17}$, $R^{18}$, $R^{19}$, and $R^{20}$ each independently represents a hydrogen atom, a halogen atom, a lower alkyl group having 1 to 4 carbon atoms, a lower alkoxy group having 1 to 4 carbon atoms, or an optionally substituted phenyl group; and o represents an integer.

Specific examples thereof include bisphenol A type polycarbonates represented by the following general formula (A-1) (e.g., YUPILON E series, manufactured by Mitsubishi Gas Chemical Company, Inc.), bisphenol Z type polycarbonate resins represented by formula (A-2) (e.g., POLYCARBONATE Z series, manufactured by Mitsubishi Gas Chemical Company, Inc.), polycarbonates represented by formula (A-3) or (A-4), and copolymers or mixtures thereof. These polycarbonates desirably have a high molecular weight so as to give a photoreceptor which is less apt to have cracks or be marred.

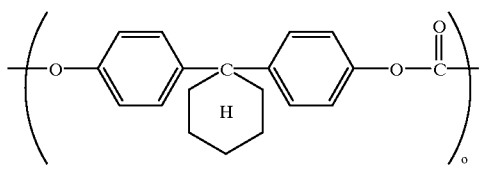
(A-2)

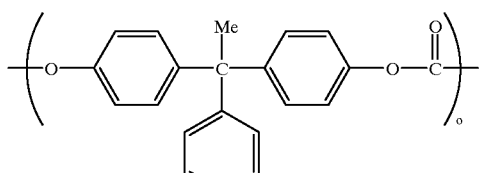
(A-3)

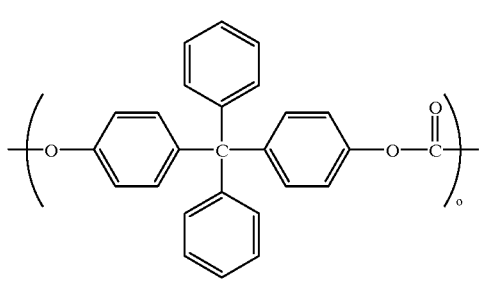
(A-4)

In the above formulae, o represents an integer.

Usable examples of the copolymers include copolycarbonates comprising a suitable combination of monomer units represented by general formula (A). Preferred examples thereof include the bisphenol/biphenol type copolycarbonate resins disclosed in JP-A-4-179961, which are represented by general formula (B):

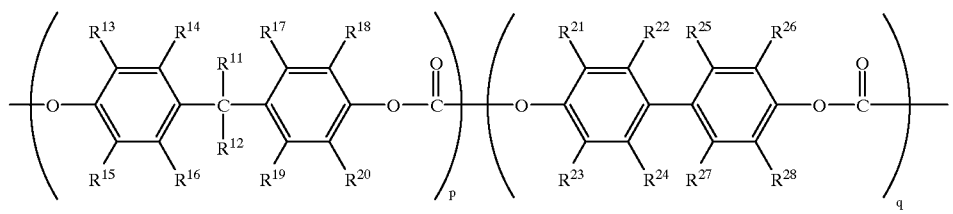
(B)

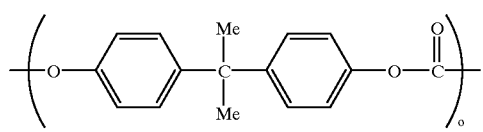
(A-1)

wherein $R^{11}$ and $R^{12}$ each independently represents a hydrogen atom, a lower alkyl group having 1 to 4 carbon atoms, a lower alkoxy group having 1 to 4 carbon atoms, or an optionally halogen-substituted phenyl group, provided that $R^{11}$ and $R^{12}$ may be bonded to each other to form a ring; $R^{13}$, $R^{14}$, $R^{15}$, $R^{16}$, $R^{17}$, $R^{18}$, $R^{19}$, and $R^{20}$ each independently represents a hydrogen atom, a halogen atom, a lower alkyl group having 1 to 4 carbon atoms, a lower alkoxy group having 1 to 4 carbon atoms, or an optionally substituted phenyl group; $R^{21}$, $R^{22}$, $R^{23}$, $R^{24}$, $R^{25}$, $R^{26}$, $R^{27}$, and $R^{28}$ each independently represents a hydrogen atom, a halogen atom, a lower alkyl group having 1 to 4 carbon atoms, a lower alkoxy group having 1 to 4 carbon atoms, or an optionally substituted phenyl group, provided that $R^{21}$, $R^{22}$, $R^{23}$, $R^{24}$, $R^{25}$, $R^{26}$, $R^{27}$, and $R^{28}$ each may be bonded to another to form a ring; and p and q each represents an integer.

Specific examples of such bisphenol copolycarbonates include bisphenol A/biphenol type polycarbonate resins represented by the following structural formulae (B-1, B-2, B-3, and B-4). (In these formulae, r and s each represents an integer; although the ratio of r to s may be any desired value, r/(r+s) is preferably from 0.1 to 0.9, more preferably from 0.7 to 0.9.)

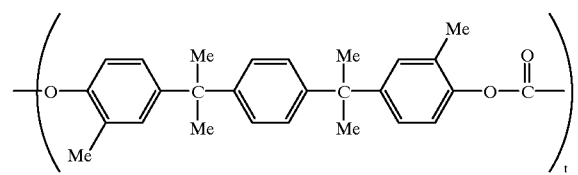

wherein t represents an integer.

Furthermore, the polycarbonates disclosed in JP-A-6-222581 can be used which are represented by the following general formula (D):

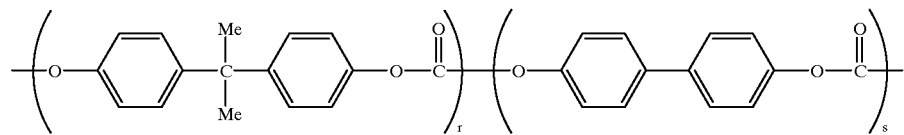

(B-1)

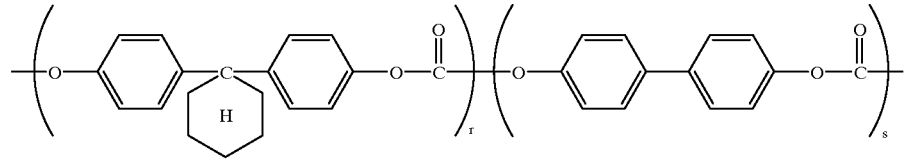

(B-2)

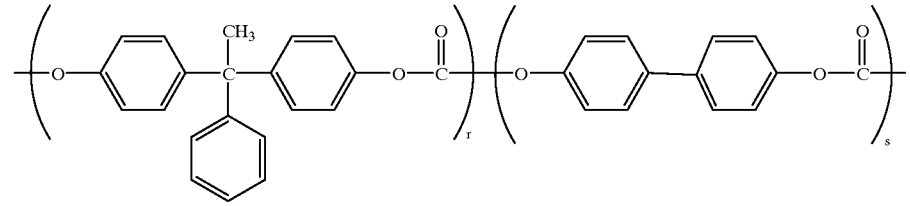

(B-3)

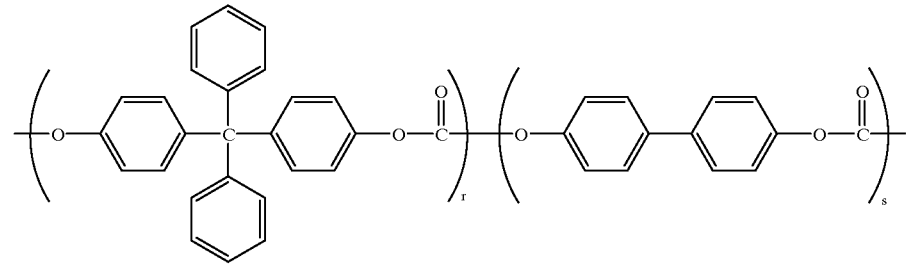

(B-4)

Also usable besides the above-described polycarbonates are the polycarbonates disclosed in JP-A-6-214412 which comprise repeating units represented by the following structural formula (C):

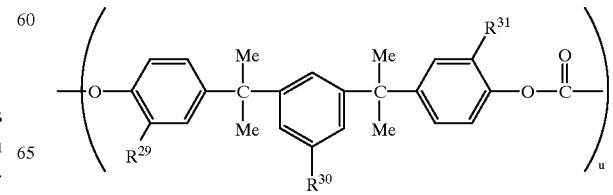

(D)

wherein $R^{29}$, $R^{30}$, and $R^{31}$ each independently represents a hydrogen atom, a halogen atom, a lower alkyl group having 1 to 4 carbon atoms, a three- to eight-membered alicyclic group containing one or more carbon atoms, a phenyl group which may be substituted with at least one substituent selected from lower alkyl groups having 1 to 4 carbon atoms, lower alkoxy groups having 1 to 4 carbon atoms, and halogen atoms, or a benzyl group which may be substituted with at least one substituent selected from lower alkyl groups having 1 to 4 carbon atoms, lower alkoxy groups having 1 to 4 carbon atoms, and halogen atoms; and u represents an integer.

A compound represented by general formula (1) of the present invention may be mixed with such a binder in any desired proportion. However, the amount of the charge-transporting material is generally from 10 to 1,000 parts by weight, preferably from 30 to 500 parts by weight, more preferably from 40 to 200 parts by weight, per 100 parts by weight of the binder.

The thickness of the charge-transporting layer obtained is generally from 2 to 40 µm. However, it is preferably from 5 to 40 µm, more preferably from 10 to 30 µm.

An organic solvent may be used without particular limitations. Examples of the solvent include alcohols such as methanol, ethanol, and isopropanol, ketones such as acetone, methyl ethyl ketone, and cyclohexanone, amides such as N,N-dimethylformamide and N,N-dimethylacetamide, sulfoxides such as dimethyl sulfoxide, ethers such as tetrahydrofuran, dioxane, and ethylene glycol dimethyl ether, esters such as ethyl acetate and methyl acetate, halogenated aliphatic hydrocarbons such as methylene chloride, chloroform, 1,2-dichloroethane, dichloroethylene, trichloroethylene, trichloroethane, and carbon tetrachloride, and aromatic compounds such as benzene, toluene, xylene, chlorobenzene, and dichlorobenzene. These solvents may be used alone or as a mixture thereof.

In the case where a charge-transporting layer is formed by coating, use can be made of coating techniques such as dip coating, spray coating, spinner coating, wire-wound bar coating, blade coating, roller coating, and curtain coating.

After the coating, the coating fluid applied is preferably dried first at room temperature and then with heating. In general, the drying with heating is preferably conducted at a temperature of from 30 to 200° C. for 5 minutes to 2 hours with or without air blowing.

Examples of the conductive support for use in the photoreceptor of the present invention include a sheet or drum form support constituted of a foil or sheet of a metal, e.g., copper, aluminum (including alumite), silver, iron, zinc, or nickel, or of an alloy thereof; a support obtained by depositing any of these metals on a plastic film or cylinder by vacuum deposition or electroplating; and a support obtained by forming a layer of a conductive compound, e.g., a conductive polymer, indium oxide, or tin oxide, on a sheet or drum form substrate such as glass, paper, or a plastic film by coating or vapor deposition.

For forming the charge-generating layer, use may be made of one or more materials selected from inorganic charge-generating materials, e.g., selenium, selenium-tellurium, and amorphous silicon, and organic charge-generating substances, e.g., cationic dyes such as pyrylium salt dyes, thiapyrylium salt dyes, azulenium salt dyes, thiacyanine dyes, and quinocyanine dyes, squarylium salt pigments, phthalocyanine pigments, polycyclic quinone pigments such as anthanthrone pigments, dibenzpyrenequinone pigments, and pyranthrone pigments, indigo pigments, quinacridone pigments, azo pigments, and pyrrolopyrrole pigments. These materials may be used alone or in combination to form a layer thereof by vapor deposition or coating.

Especially preferred among the organic charge-generating substances enumerated above are the organic charge-generating substances described in Chem. Rev., 1993, 93, pp. 449–486.

Specific examples of the phthalocyanine pigments include alkoxytitanium phthalocyanines (Ti(OR)$_2$Pc), oxotitanium phthalocyanine (TiOPc), copper phthalocyanine (CuPc), metal-free phthalocyanine (H$_2$Pc), hydroxygallium phthalocyanine (HOGaPc), vanadyl phthalocyanine (VOPc), and chloroindium phthalocyanine (ClInPc). More specifically, examples of the TiOPc include α-TiOPc, β-TiOPc, γ-TiOPc, m-TiOPc, Y-TiOPc, A-TiOPc, B-TiOPc, and amorphous TiOPc, and examples of the H$_2$Pc include α-H$_2$Pc, β-H$_2$Pc, τ1-H$_2$Pc, τ2-H$_2$Pc, and x-H$_2$Pc.

Two or more of these phthalocyanines may be mixed with each other by milling and used as a mixture or as a new mixed-crystal system. For example, use may be made of an oxotitanyl phthalocyanine/vanadyl phthalocyanine mixed crystal described, e.g., in JP-A-4-371962, JP-A-5-2278, and JP-A-5-2279 and an oxotitanyl phthalocyanine/chloroindium phthalocyanine mixed crystal described, e.g., in JP-A-6-148917, JP-A-6-145550, JP-A-6-271786, and JP-A-5-297617.

Examples of the azo compounds include monoazo pigments, bisazo pigments, trisazo pigments, and tetrakisazo pigments. Especially preferred of these are the compounds represented by the following structural formulae.

Bisazo Compounds

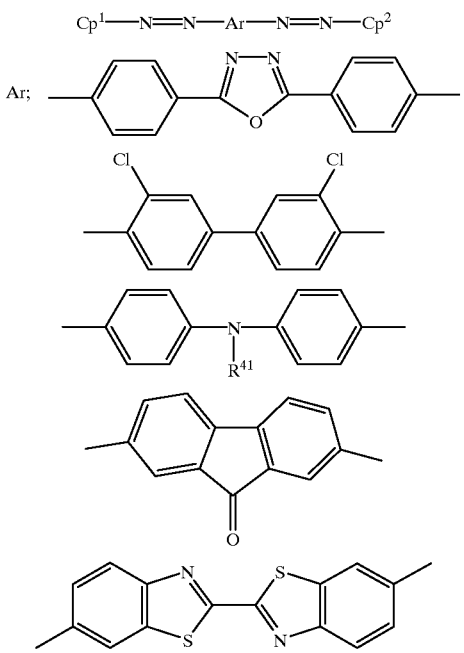

(In the above formulae, $R^{41}$ represents a lower alkyl group.)

Trisazo Compounds

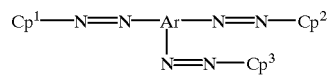

-continued

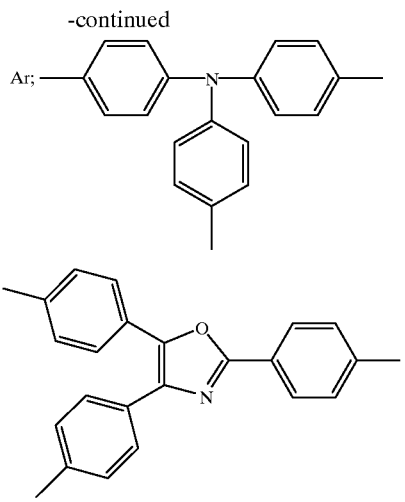

Cp¹ and Cp² in the bisazo compounds and Cp¹, Cp², and Cp³ in the trisazo compounds each represents any of the following.

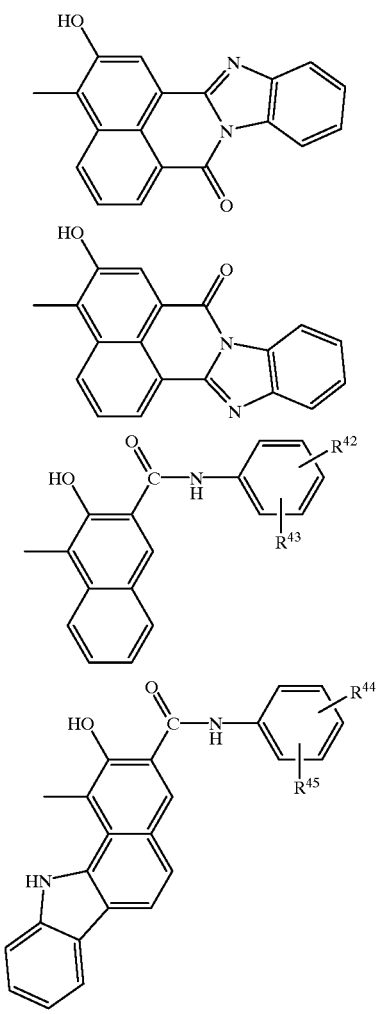

(In the above formulae, R⁴², R⁴³, R⁴⁴, and R⁴⁵ may be the same or different, and each represents a hydrogen atom, a halogen atom, or a lower alkyl group.)

The perylene or polycyclic quinone compounds represented by the following structural formulae are also preferred.

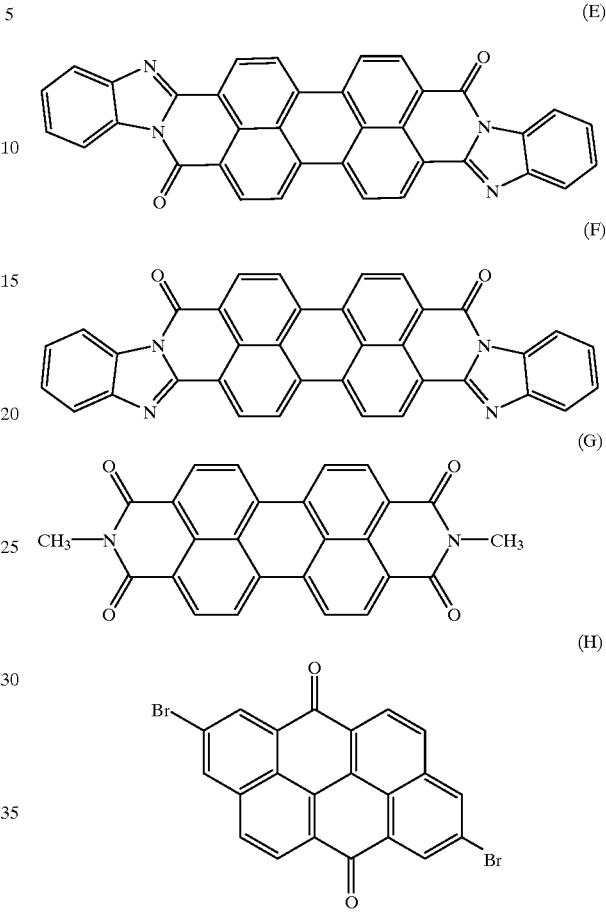

Besides those substances, any material can be used as long as it generates charges at a high efficiency upon light absorption.

If desired and necessary, other charge-transporting materials and various additives can be incorporated into the charge-transporting layer in the present invention. Examples of the optionally usable charge-transporting materials include diaminobiphenyl compounds represented by the following general formula (2):

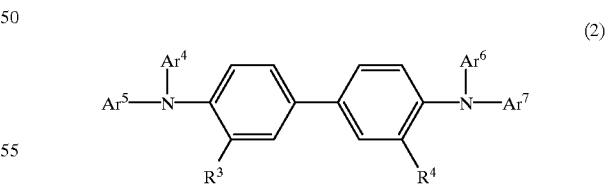

wherein $R^3$ and $R^4$ may be the same or different and each represents a hydrogen atom, a halogen atom, a lower alkyl group having 1 to 4 carbon atoms, a lower alkoxy group having 1 to 4 carbon atoms, or a phenyl group; $Ar^4$, $Ar^5$, $Ar^6$, and $Ar^7$ may be the same or different and each represents a phenyl group which may have one or more substituents selected from halogen atoms, lower alkyl groups having 1 to 4 carbon atoms, and lower alkoxy groups having 1 to 4 carbon atoms or an optionally substituted α-naphthyl, β-naphthyl, or biphenyl group.

Especially preferred among these are the diaminobiphenyl compounds represented by the following general formula (3) and that represented by the following formula (4):

(3)

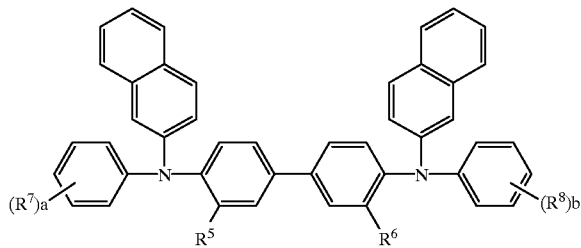

wherein $R^5$, $R^6$, $R^7$, and $R^8$ may be the same or different and each represents a hydrogen atom, a halogen atom, a lower alkyl group having 1 to 4 carbon atoms, a lower alkoxy group having 1 to 4 carbon atoms, or a phenyl group; and a and b each represents an integer of 1 or 2.

(4)

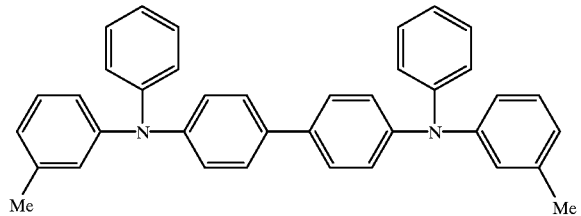

Examples of the optionally usable charge-transporting materials further include the hydrazone compounds represented by the following general formula (I) which are described, e.g., in JP-B-55-42380, JP-A-60-340999, and JP-A-61-23154, the distyryl compounds represented by the following general formula (J) which are described, e.g., in U.S. Pat. No. 3,873,312, tetraphenylbutadiene compounds, α-phenylstilbene, polyvinylcarbazole, and triphenylmethane. However, the optionally usable charge-transporting materials should not be construed as being limited to these examples:

(I)

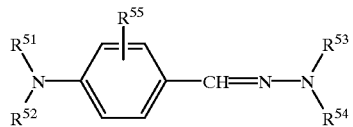

wherein $R^{51}$ and $R^{52}$ may be the same or different and each represents an optionally substituted lower alkyl group, an optionally substituted aryl group, or an optionally substituted aralkyl group; $R^{53}$ and $R^{54}$ may be the same or different and each represents an optionally substituted lower alkyl group, an optionally substituted aryl group, an optionally substituted aralkyl group, or an optionally substituted heterocyclic group, provided that $R^{53}$ and $R^{54}$ may be bonded to each other to form a ring; and $R^{55}$ represents a hydrogen atom, a lower alkyl group, an optionally substituted aryl group, an optionally substituted aralkyl group, a lower alkoxy group, or a halogen atom, provided that $R^{55}$ may be bonded to $R^{51}$ or $R^{52}$ to form a ring;

(J)

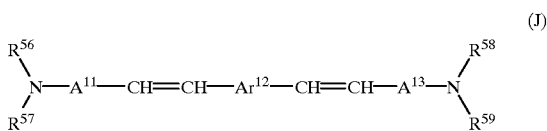

wherein $R^{56}$ to $R^{59}$ may be the same or different and each represents a lower alkyl group or an optionally substituted aryl group; $Ar^{11}$ and $Ar^{13}$ may be the same or different and each represents a phenyl group which may have one or more substituents selected from lower alkyl groups, lower alkoxy groups, aryloxy groups, and halogen atoms; and $Ar^{12}$ represents either a mono- or polycyclic aromatic group having 4 to 14 carbon atoms which may have one or more substituents selected from the same substituents as those for $Ar^{11}$ and $Ar^{13}$ or a heterocyclic group which may have one or more substituents selected from the same substituents as those for $Ar^{11}$ and $Ar^{13}$.

Various additives including, e.g., ultraviolet absorbers and antioxidants are used, if desired and necessary, in the photosensitive layer(s) in the present invention for the purpose of improving the durability of the photoreceptor. Examples of the various additives include plasticizers such as the biphenyl compounds disclosed in JP-A-6-332206, m-terphenyl, m-di-tert-butylphenyl, and dibutyl phthalate, surface lubricants such as silicone oils, silicone graft polymers, and various fluorocarbons, potential stabilizers such as dicyanovinyl compounds and carbazole derivatives, monophenol antioxidants such as 2-tert-butyl-4-methylphenol and 2,6-di-tert-butyl-4-methylphenol, bisphenol antioxidants, polymeric phenol antioxidants, amine antioxidants such as 4-diazabicyclo[2.2.2]octane, salicylic acid antioxidants, sulfur compound antioxidants such as dilauryl 3,3'-thiodipropionate, phosphorus compound antioxidants, hindered amine light stabilizers such as bis(2,2,6,6-tetramethyl-4-piperidyl) sebacate, and dl-tocopherol (vitamin E).

A protective layer can be formed on the thus-formed photosensitive layer(s) by coating if desired and necessary. Furthermore, as shown in FIG. 1b, an undercoat layer 3 functioning as both a barrier and an adhesive layer may be formed between the conductive support and the photosensitive layer(s). Examples of the material constituting the undercoat layer include poly (vinyl alcohol), nitrocellulose, casein, ethylene/acrylic acid copolymers, polyamides such as nylons, polyurethanes, gelatin, and aluminum oxide. The thickness of the undercoat layer is generally from 0.1 to 5 μm, preferably from 0.5 to 3 μm.

Thus, an electrophotographic photoreceptor can be obtained which has a charge-transporting layer containing a novel bis(3,4-methylenedioxyphenylamino) derivative (1) of the present invention.

As described above, the novel bis(3,4-methylenedioxyphenylamino) derivatives (1) of the present invention are stable after having been formed into a film and give an electrophotographic photoreceptor having excellent properties.

The present invention will be explained below in more detail by reference to the following Examples, but the invention should not be construed as being limited to these Examples. The analytical instruments and conditions shown below were used in the Examples and Comparative Examples.

(1) $^1$H-NMR Spectrometry Instrument: Type AM-400, manufactured by Bruker Inc. Solvent: $C_6D_6$, DMSO-$D_6$, or CDCl$_3$ Internal reference: tetramethylsilane (2) Mass Spectrometry
Instrument: Hitachi M-80B (manufactured by Hitachi Ltd.)

EXAMPLE 1

Synthesis of 4,4'-Bis(N-3",4"-methylenedioxyphenyl-N-phenylamino)biphenyl (Exemplified Compound 1; $Ar^1=Ar^2=Ph$, $Ar^3=4,4'$-biphenylene)

(1) Synthesis of 3,4-Methylenedioxyacetanilide (7)

Into a 5-liter reaction flask were introduced 274 g (2.0 mol) of 3,4-methylenedioxyaniline (manufactured by Tokyo Kasei Kogyo Co., Ltd.), 2 liters of water, and 230 g of concentrated hydrochloric acid. Thereto was added 250 g of acetic anhydride with stirring. Immediately thereafter, a solution prepared from 198 g of sodium acetate and 800 ml of water was added thereto (the reaction mixture was cooled with ice water because the addition resulted in heat generation). The resultant mixture was stirred at room temperature for 1 hour, and the crystals precipitated were taken out by filtration and washed with water. The crystals were taken out and recrystallized from methanol (500 ml) to obtain 188.3 g of 3,4-methylenedioxyacetanilide (7).

Yield, 52.5%; mp, 140–141° C. $^1$H-NMR (δ; ppm in $C_6D_6$): 1.43 (s, 3H), 5.28 (s, 2H), 5.59 (brs, 1H), 6.59 (d, J=8.3 Hz, 1H), 6.67 (d, J=8.3 Hz, 1H), 7.37 (s, 1H). MS: 179 ($M^+$), 137, 107, 79, 52, 43.

(2) Synthesis of 4,4'-Bis(N-3",4"-methylenedioxyphenyl-N-acetylamino)biphenyl

Into a 1-liter four-necked flask were introduced 180 g (1.005 mol) of 3,4-methylenedioxyacetanilide (7), 125 g (0.401 mol) of 4,4'-dibromobiphenyl (manufactured by Tokyo Kasei Kogyo Co., Ltd.), 20 g (0.125 mol) of copper sulfate, and 132 g (0.955 mol) of potassium carbonate. Thereto was added 500 ml of isobutylbenzene. This mixture was refluxed for 1.5 days with dehydration, subsequently cooled to 100° C., and then filtered through a Celite. The Celite was rinsed with toluene and the filtrate was concentrated to obtain about 180 g of a residue. The residue was recrystallized from chloroform/ethanol to obtain 110 g of a crude reaction product, which was recrystallized from chlorobenzene in order to further heighten the purity. Thus, 98.3 g of the target compound was obtained. The Celite was further rinsed with chloroform because the target compound still remained thereon. The crude reaction product thus recovered in an amount of about 90 g was recrystallized from chlorobenzene to obtain 21.1 g of the target compound. As a result, the target compound was obtained in a total amount of 119.4 g.

Yield, 58.6%; mp, 209–210° C. $^1$H-NMP (δ; ppm in DMSO-$D_6$): 1.95 (s, 6H), 6.04 (s, 4H), 6.80–6.94 (m, 4H), 7.03 (s, 2H), 7.40 (d, J=8.5 Hz, 4H), 7.62 (d, J=8.5 Hz, 4H). MS: 508 ($M^+$), 466, 424, 371, 305, 287, 162, 136.

(3) Synthesis of 4,4'-Bis(N-3",4"-methylenedioxyphenylamino)biphenyl

In 100 ml of dimethyl sulfoxide (DMSO) was dissolved 40.0 g (78.7 mmol) of 4,4'-bis(N-3",4"-methylenedioxyphenyl-N-acetylamino)biphenyl with heating. Methanol was added thereto in the same amount. While this mixture was held at 60° C., 26 g (393.9 mmol) of 85% potassium hydroxide was gradually added thereto over 30 minutes. The resultant mixture was stirred at that temperature for 3 hours to concentrate the methanol. This reaction mixture was poured into 1.6 liters of water. The resultant precipitate was taken out by filtration, washed with water, and then dissolved in hot toluene. The resultant black insoluble matter was removed by filtration through a filter paper. The filtrate was heated to concentrate the toluene to some degree and then allowed to stand at room temperature to conduct recrystallization. Thus, 26.38 g of the target compound was obtained.

Yield, 79.0%; mp, 176–180° C. $^1$H-NMR (δ; ppm in $C_6D_6$): 4.85 (brs, 2H), 5.35 (s, 4H), 6.37 (dd, J=8.2 Hz, J=2.2 Hz, 2H), 6.61 (d, J=2.2 Hz, 2H), 6.62 (d, J=8.3 Hz, 2H), 6.83 (d, J=8.6 Hz, 4H), 7.44 (d, J=8.7 Hz, 4H) MS: 424 ($M^+$), 304, 212, 154, 136.

(4) Synthesis of 4,4'-Bis(N-3",4"-methylenedioxyphenyl-N-phenylamino)biphenyl (Exemplified Compound 1)

Into a 200-ml four-necked flask were introduced 3.0 g (7.068 mmol) of 4,4'-bis(N-3",4"-methylenedioxyphenylamino)biphenyl, 60 ml of iodobenzene, 200 mg (3.15 mmol) of a copper powder, and 2 g (14.17 mmol) of potassium carbonate. This mixture was refluxed for 7 hours with dehydration, subsequently cooled to about 100° C., and then filtered through a Celite. The Celite was rinsed with toluene and the filtrate was concentrated. The residue was purified by silica gel column chromatography (solvent: toluene) to obtain 3.4 g of an oily substance, which was crystallized from ethyl acetate. As a result, 2.8 g of Exemplified Compound 1 was obtained.

Yield, 79.2%; mp, 145–148° C. $^1$H-NMR (δ; ppm in $C_6D_6$): 5.28 (s, 4H), 6.53 (m, 4H), 6.75 (s, 2H), 6.84 (m, 2H), 7.03–7.16 (m, 12H), 7.38 (d, J=8.7 Hz, 4H). MS: 576 ($M^+$), 288.

EXAMPLE 2

Synthesis of 4,4'-Bis(N-3",4"-methylenedioxyphenyl-N-p-tolylamino)biphenyl (Exemplified Compound 2; $Ar^1=Ar^2=$ p-tolyl, $Ar^3=4,4'$-biphenylene)

A mixture of 31.6 g (74.5 mmol) of 4,4'-bis(N-3",4"-methylenedioxyphenylamino)biphenyl, 300 ml (2.54 mol) of p-iodotoluene, 2.4 g (37.8 mmol) of a copper powder, 24 g (173.7 mmol) of potassium carbonate, and 200 ml of isobutylbenzene was refluxed for 43 hours with dehydration. The resultant reaction mixture was treated in the same manner as in Example 1 (4). The residue was purified by silica gel column chromatography (solvent: toluene) to obtain 33.0 g of a reaction product, which was recrystallized from ethyl acetate. As a result, 25.1 g of Exemplified Compound 2 was obtained.

Yield, 55.8%; mp, 198–199° C. $^1$H-NMR (δ; ppm in $C_6D_6$): 2.12 (s, 6H), 5.33 (s, 4H), 6.57 (s, 4H), 6.78 (s, 2H), 6.91 (d, J=8.5 Hz, 4H), 7.07 (d, J=8.4 Hz, 4H), 7.13 (d, J=8.7 Hz, 4H), 7.38 (d, J=8.7 Hz, 4H).

MS: 604 ($M^+$), 378, 302, 97, 73, 45.

EXAMPLE 3

Synthesis of 4,4'-Bis(N-3",4"-methylenedioxyphenyl-N-m-tolylamino)biphenyl (Exemplified Compound 3; $Ar^1=Ar^2=$ m-tolyl, $Ar^3=4,4'$-biphenylene)

A mixture of 5.0 g (11.8 mmol) of 4,4'-bis(N-3",4"-methylenedioxyphenylamino)biphenyl, 50 ml (0.39 mol) of m-iodotoluene, 400 mg (6.3 mmol) of a copper powder, 3.8 g (27.5 mmol) of potassium carbonate, and 40 ml of diisopropylbenzene was refluxed for 10 hours with dehydration. The resultant reaction mixture was treated in the same manner as in Example 1 (4). The residue was purified by silica gel column chromatography (solvent: toluene) to obtain 5.78 g of a reaction product, which was recrystallized from ethyl acetate and ethanol. As a result, 1.78 g of Exemplified Compound 3 was obtained.

Yield, 25.0%; mp, 149–152° C. $^1$H-NMR (δ; ppm in $C_6D_6$): 2.03 (s, 6H), 5.30 (s, 4H), 6.57 (s, 4H), 6.71 (d, J=7.3 Hz, 2H), 6.79 (m, 2H), 6.95–7.06 (m, 6H), 7.15 (m, 4H), 7.39 (d, J=8.8 Hz, 4H). MS: 604 ($M^+$), 378, 302.

EXAMPLE 4

Synthesis of 4,4'-Bis(N-3",4"-methylenedioxyphenyl-N-2'",4'"-dimethylphenylamino)biphenyl (Exemplified Compound 4; $Ar^1=Ar^2=2,4$-dimethylphenyl, $Ar^3=4,4'$-biphenylene)

A mixture of 5.0 g (11.8 mmol) of 4,4'-bis(N-3",4"-methylenedioxyphenylamino)biphenyl, 35 ml (0.25 mol) of 4-iodo-m-xylene, 400 mg (6.3 mmol) of a copper powder, 3.8 g (27.5 mmol) of potassium carbonate, and 40 ml of diisopropylbenzene was refluxed for 15 hours with dehydration. The resultant reaction mixture was treated in the same manner as in Example 1 (4). The residue was purified by silica gel column chromatography (solvent: toluene) to obtain 6.3 g of a reaction product, which was recrystallized from ethyl acetate. As a result, 3.2 g of Exemplified Compound 4 was obtained.

Yield, 42.9%; mp, 222–224° C. $^1$H-NMR (δ; ppm in $C_6D_6$): 2.05 (s, 6H), 2.15 (s, 6H), 5.30 (s, 4H), 6.49 (dd, J=8.4 Hz, J=2.2 Hz, 2H), 6.55 (d, J=8.3 Hz, 2H), 6.79 (d, J=2.2 Hz, 2H), 6.82–6.89 (m, 4H), 7.00 (d, J=8.8 Hz, 4H), 7.03 (d, J=8.0 Hz, 2H), 7.38 (d, J=8.8 Hz, 4H). MS: 632 ($M^+$), 392, 316.

EXAMPLE 5
Synthesis of 4,4'-Bis(N-3",4"-methylenedioxyphenyl-N-4'''-ethylphenylamino)biphenyl (Exemplified Compound 5; $Ar^1=Ar^2$=p-ethylphenyl, $Ar^3$=4,4'-biphenylene)

(1) Synthesis of 4-Ethylacetanilide

Into a 10-liter reaction flask were introduced 243.8 g (2.01 mol) of 4-ethylaniline, 2 liters of water, 230 g of concentrated hydrochloric acid, and 250 g of acetic anhydride. A solution prepared by dissolving 200 g of sodium acetate in 800 ml of water was added dropwise thereto at 10 to 20° C. This mixture was stirred overnight at room temperature, and the resultant precipitate was taken out by filtration. The crystals were washed with water and recrystallized from methanol (200 ml) to obtain 150 g of the target compound.

Yield, 45.7%; mp, 86–87° C. $^1$H-NMR (δ; ppm in $C_6D_6$): 1.07 (t, J=7.6 Hz, 3H), 1.60 (s, 3H), 2.42 (q, J=7.6 Hz, 2H), 6.88 (brs, 1H), 7.00 (d, J=8.3 Hz, 2H), 7.53 (d, J=8.4 Hz, 2H). MS: 163 ($M^+$), 121, 106, 77, 43.

(2) Synthesis of 4-Ethyl-3',4'-methylenedioxydiphenylamine

A mixture of 50 g (306.3 mmol) of 4-ethylacetanilide, 80 g (398.0 mmol) of 3,4-methylenedioxybromobenzene, 8.2 g of copper sulfate, and 50 g of potassium carbonate was reacted in 500 ml of isobutylbenzene with refluxing for one day. The reaction mixture was filtered through a Celite and the filtrate was concentrated. Thereto were added 300 ml of methanol and 130 g of 85% potassium hydroxide. This mixture was refluxed for 3 hours and concentrated. Thereafter, water was added thereto and the resultant mixture was extracted with toluene. The extract was dried with magnesium sulfate and then concentrated. The residue was distilled under vacuum to obtain 64.4 g of an oily substance (160–165° C./1 mmHg). This oily substance was crystallized from hexane to obtain 59.2 g of white crystals.

Yield, 80.1%; mp, 38–39° C. $^1$H-NMR (δ; ppm in $C_6D_6$): 1.16 (t, J=7.6 Hz, 3H), 2.46 (q, J=7.6 Hz, 2H), 4.80 (brs, 1H), 5.33 (s, 2H), 6.30 (d, J=8.3 Hz, 1H), 6.55 (s, 1H), 6.60 (d, J=8.3 Hz, 1H), 6.77 (d, J=8.5 Hz, 2H), 6.95 (d, J=8.5 Hz, 2H). MS: 241 ($M^+$), 226, 212, 196, 182, 167, 154, 141, 128, 115, 105, 91.

(3) Synthesis of 4,4'-Bis(N-3",4"-methylenedioxyphenyl-N-4'''-ethylphenylamino)biphenyl (Exemplified Compound 5)

A mixture of 8.0 g (33.2 mmol) of 4-ethyl-3',4'-methylenedioxydiphenylamine, 5.6 g (13.8 mmol) of 4,4'-diiodobiphenyl, 550 mg (0.70 mmol) of $PdCl_2[P(o\text{-tolyl})_3]_2$, 3.7 g (38.5 mmol) of sodium tert-butoxide, and 50 ml of toluene was stirred overnight at 60° C. in a nitrogen stream. This mixture was washed with 100 ml of water, dried ($MgSO_4$), and then concentrated. The residue was purified by silica gel column chromatography (solvent: hexane/toluene=1/1) to obtain 6.01 g of a crude reaction product, which was recrystallized from ethanol/acetone. As a result, 4.90 g of Exemplified Compound 5 was obtained.

Yield, 56.1%; mp, 159–160° C. $^1$H-NMR (δ; ppm in $C_6D_6$): 1.10 (t, J=7.6 Hz, 6H), 2.45 (q, J=7.6 Hz, 4H), 4.80 (brs, 1H), 5.30 (s, 4H), 6.57 (m, 4H), 6.80 (m, 2H), 6.96 (d, J=8.6 Hz, 4H), 7.11 (d, J=8.0 Hz, 4H), 7.15 (m, 4H), 7.39 (d, J=8.8 Hz, 4H). MS: 632 ($M^+$), 392, 316.

EXAMPLE 6
Synthesis of 4,4'-Bis(N-3",4"-methylenedioxyphenyl-N-p-tolylamino-3,3'-dimethylbiphenyl (Exemplified Compound 12; $Ar^1=Ar^2$=p-tolyl, $Ar^3$=3,3'-dimethyl-4,4"-biphenyl)

(1) Synthesis of 4,4'-Bis(N-3",4"-methylenedioxyphenylamino)-3,3'-dimethylbiphenyl A mixture of 10 g (33.7 mmol) of 3,3'-dimethyl-4,4'-diacetylaminobiphenyl, 20 g (99.5 mmol) of 3,4-methylenedioxybromobenzene, 2.5 g (15.7 mmol) of copper sulfate, 17 g of potassium carbonate, and 200 ml of isobutylbenzene was refluxed for 1 day with dehydration. This mixture was filtered through a Celite and then concentrated. To the crude reaction product (4,4'-bis[N-(3",4"-methylenedioxyphenyl)-N-acetylamino]-3,3'-dimethylbiphenyl) were added 20 g of 85% potassium hydroxide and methanol/DMSO (50 ml/50 ml). This mixture was reacted at 80° C. overnight and then poured into water. The resultant precipitate was recrystallized from dioxane to obtain 10.0 g of the target compound.

Yield, 65.6%; mp, 235–240° C. $^1$H-NMR (δ; ppm in DMSO-$D_6$): 2.25 (s, 6H), 3.20 (s, 2H), 5.94 (s, 4H), 6.42 (dd, J=8.3 Hz, J=2.2 Hz, 2H), 6.58 (d, J=2.1 Hz, 2H), 6.77 (d, J=8.3 Hz, 2H), 7.02 (s, 2H), 7.05 (d, J=8.4 Hz, 2H), 7.30 (dd, J=8.3 Hz, J=2.3 Hz, 2H), 7.40 (d, J=2.0 Hz, 2H). MS: 452 ($M^+$), 226, 136, 91.

(2) Synthesis of 4,4'-Bis(N-3",4"-methylenedioxyphenyl-N-p-tolylamino)-3,3'-dimethylbiphenyl (Exemplified Compound 12)

A mixture of 3.0 g (6.63 mmol) of 4,4'-bis(N-3",4"-methylenedioxyphenylamino)-3,3'-dimethylbiphenyl, 30 ml (233.9 mmol) of p-iodotoluene, 210 mg (3.30 mmol) of copper, 2.3 g (16.6 mmol) of potassium carbonate, and 20 ml of diisopropylbenzene was refluxed for 1 day with dehydration. The resultant reaction mixture was treated in the same manner as in Example 1 (4). The crude reaction product thus obtained was purified by column chromatography ($SiO_2$, solvent: toluene/hexane=1/1) and then crystallized from an ethanol/acetone mixed solvent. As a result, 1.47 g of the target compound was obtained.

Yield, 35.0%; mp, 122–124° C. $^1$H-NMR (δ; ppm in $C_6D_6$): 2.12 (s, 6H), 2.13 (s, 6H), 5.30 (s, 4H), 6.48 (dd, J=8.4 Hz, J=2.2 Hz, 2H), 6.57 (d, J=8.3 Hz, 2H), 6.79 (d, J=2.2 Hz, 2H), 6.90 (d, J=8.2 Hz, 4H), 6.98 (d, J=8.6 Hz, 4H), 7.1–7.2 (2H), 7.34 (dd, J=7.8 Hz, J=1.9 Hz, 2H), 7.43 (d, J=2.1 Hz, 2H). MS: 632 ($M^+$), 316.

EXAMPLE 7
Synthesis of 1,3-Bis(N-3',4'-methylenedioxyphenyl-N-p-tolylamino)benzene (Exemplified Compound 17; $Ar^1=Ar^2$=p-tolyl, $Ar^3$=m-phenylene)

(1) Synthesis of Diacetyl-m-phenylenediamine

Into a 1-liter reaction flask cooled with an ice bath was introduced 35 ml of acetic acid. Thereto was gradually added 15 g (138.7 mmol) of m-phenylenediamine. Thereto was dropwise added 2 ml (307.4 mmol) of acetic anhydride at room temperature to 30° C. After completion of the addition, the mixture was stirred at 60° C. for 1 hour and then poured into 150 ml of water. The resultant precipitate was taken out by filtration, sufficiently washed with water, and then dried to obtain 18.4 g of diacetyl-m-phenylenediamine as the target compound.

Yield, 70.7%; mp, 184–185° C. MS: 192, 150, 108, 80, 43.

(2) Synthesis of 1,3-Bis(N-3',4'-methylenedioxyphenyl-N-acetylamino)benzene

A mixture of 4.9 g (25.5 mmol) of diacetyl-m-phenylenediamine, 20.0 g (99.5 mmol) of 3,4-methylenedioxybromobenzene, 1.6 g of a copper powder, 7.0 g of potassium carbonate, and 100 ml of nitrobenzene was refluxed for 8 hours with dehydration. The reaction mixture was cooled and then filtered through a Celite. The filtrate was concentrated with a vacuum pump (bath, 90° C.). The concentrate was purified with a silica gel column (solvent: ethyl acetate) to obtain 3.0 g of a crude reaction product (26.5%), which was recrystallized from ethyl acetate/toluene to obtain 2.29 g of 1,3-bis(N-3',4'-methylenedioxyphenyl-N-acetylamino)benzene.

Yield, 20.2%; mp, 213–215° C. MS: 432, 390, 348, 211, 162, 136.

(3) Synthesis of 1,3-Bis(N-3',4'-methylenedioxyphenylamino)benzene

Ten grams (23.1 mmol) of 1,3-bis(N-3',4'-methylenedioxyphenyl-N-acetylamino)benzene was subjected to methanolysis in the same manner as in Example 1 (3). The reaction mixture was poured into water, and this mixture was extruded with toluene. The extract was dried (magnesium sulfate), concentrated, and then purified by silica gel column chromatography (toluene/ethyl acetate=5/1) to obtain 6.1 g of an oily substance. This oily substance was crystallized from isopropanol to obtain 5.2 g of 1,3-bis (N-3',4'-methylenedioxyphenylamino)benzene as white crystals.

Yield, 64.6%; mp, 91–92° C. $^1$H-NMR (δ; ppm in CDCl$_3$): 5.43 (brs, 2H), 5.92 (s, 4H), 6.43 (dd, J=8.0 Hz, J=2.2 Hz, 2H), 6.47 (t, J=2.1 Hz, 1H), 6.54 (dd, J=8.2 Hz, J=2.2 Hz, 2H), 6.69 (d, J=2.2 Hz, 2H), 6.73 (d, J=8.2 Hz, 2H), 7.05 (d, J=8.0 Hz, 1H). MS: 348, 154.

(4) Synthesis of 1,3-Bis(N-3',4'-methylenedioxyphenyl-N-p-tolylamino)benzene (Exemplified Compound 17)

A mixture of 2.0 g (5.7 mmol) of 1,3-bis(N-3',4'-methylenedioxyphenylamino)benzene, 3.7 g (17.0 mmol) of p-iodotoluene, 100 mg (1.57 mmol) of a copper powder, and 2.0 g (14.5 mmol) of potassium carbonate was reacted in 50 ml of diisopropylbenzene for 5 hours with refluxing and dehydration. The resultant reaction mixture was treated in the same manner as in Example 1 (4). The residue was purified by silica gel column chromatography (solvent: toluene) to obtain 2.41 g of crystals, which were recrystallized from a hexane/toluene (10 ml/10 ml) mixed solvent. As a result, 1.98 g of crystals of Exemplified Compound 17 were obtained.

Yield, 65.7 %; mp, 139–140 ° C. $^1$H-NMR (δ; ppm in C$_6$D$_6$): 2.06 (s, 6H), 5.26 (s, 4H), 6.49 (d, J=8.3 Hz, 2H), 6.54 (dd, J=8.4 Hz, 2.1 Hz, 2H), 6.71 (dd, J=8.0 Hz, J=2.2 Hz, 2H), 6.73 (d, J=2.1 Hz, 2H), 6.85 (d, J=8.1 Hz, 4H), 6.95 (t, J=8.1 Hz, 1H), 7.03 (d, J=8.5 Hz, 4H), 7.01–7.06 (m, 1H).
MS: 528, 302, 105, 44.

EXAMPLE 8

Synthesis of 1,3-Bis(N-3',4'-methylenedioxyphenyl-N-2",4"-dimethylphenylamino)benzene (Exemplified Compound 19; Ar$^1$=Ar$^2$=2,4-dimethylphenyl, Ar$^3$=m-phenylene)

A mixture of 2.0 g (5.7 mmol) of 1,3-bis(N-3',4'-methylenedioxyphenylamino)benzene, 4.0 g (17.2 mmol) of p-iodo-m-xylene, 100 mg (1.57 mmol) of a copper powder, and 2.0 g (14.5 mmol) of potassium carbonate was reacted in 50 ml of diisopropylbenzene for 8 hours with refluxing and dehydration. The resultant reaction mixture was treated in the same manner as in the synthesis of Exemplified Compound 17. As a result, 1.82 g of crystals of Exemplified Compound 19 were obtained.

Yield, 57.4%; mp, 153–154° C. $^1$H-NMR (δ; ppm in C$_6$D$_6$): 2.05 (s, 6H), 2.09 (s, 6H), 5.28 (s, 4H), 6.45–6.53 (m, 6H), 6.71 (d, J=2.1 Hz, 2H), 6.78–6.84 (m, 5H), 6.91 (t, J=8.0 Hz, 1H), 7.02 (d, J=7.9 Hz, 2H). MS: 556, 316, 278, 238, 210, 182.

EXAMPLE 9

Synthesis of 1,3-Bis(N-3',4'-methylenedioxyphenyl-N-2"-naphthylamino)benzene (Exemplified Compound 21; Ar$^1$=Ar$^2$=β-naphthyl, Ar$^3$=m-phenylene)

(1) Synthesis of N,N'-Di-2-naphthyl-m-phenylenediamine

Into a 100-ml reaction flask were introduced 5.0 g (46.2 mmol) of m-phenylenediamine, 20.1 g (97.1 mmol) of 2-bromonaphthalene, 222 mg of Pd$_2$ (dba)$_3$, i.e., tris (dibenzylideneacetone)dipalladium, 269 mg of 1,1-bis (diphenylphosphino)ferrocene, and 9.5 g (98.9 mmol) of sodium t-butoxide. After the atmosphere in the flask was replaced with nitrogen, 20 ml of toluene was added to the contents. This mixture was reacted at 120° C. overnight. The reaction mixture was cooled to room temperature and the resultant inorganic salt precipitate was filtered off. The filtrate was washed with water (twice), dried (MgSO$_4$), and then concentrated. The resultant crude crystals were recrystallized from toluene to obtain 7.03 g of the target compound.

Yield, 42.2%; mp, 191–192° C. $^1$H-NMR (δ; ppm in CDCl$_3$): 5.87 (s, 2H), 6.77 (dd, J=8.0 Hz, J=2.2 Hz, 2H), 6.96 (t, J=2.0 Hz, 1H), 7.16–7.50 (m, 10H), 7.65–7.50 (m, 6H). MS: 360, 231, 217, 204, 180, 128, 115, 65.

(2) Synthesis of 1,3-Bis(N-3',4'-methylenedioxyphenyl-N-2"-naphthylamino)benzene (Exemplified Compound 21)

Into a 50-ml flask were introduced 3.0 g (8.3 mmol) of N,N'-di-2-naphthyl-m-phenylenediamine, 4.0 g (19.9 mmol) of 3,4-methylenedioxybromobenzene, 10 mg (0.045 mmol) of palladium acetate, 60 mg (0.197 mmol) of (tri-o-tolyl) phosphine, and 2.0 g (20.8 mmol) of sodium t-butoxide. Thereto was added 20 ml of toluene. This mixture was reacted at 100° C. overnight and then filtered. The filtrate was washed with water, dried (magnesium sulfate), and then concentrated. The concentrate was crystallized from toluene/hexane. The resultant crystals (2.49 g) were purified with a silica gel column (toluene), and this purified reaction product (2.49 g) was recrystallized from toluene/hexane. As a result, 2.04 g of Exemplified Compound 21 was obtained.

Yield, 40.9%; mp, 166–168° C. $^1$H-NMR (δ; ppm in C$_6$D$_6$): 6.49 (d, J=8.3 Hz, 2H), 6.55 (dd, J=8.3 Hz, J=2.3 Hz, 2H), 6.75 (d, J=2.1 Hz, 2H), 6.78 (dd, J=8.0 Hz, J=2.0 Hz, 2H), 6.98 (t, J=8.1 Hz, 1H), 7.11–7.18 (m, 5H), 7.29 (dd, J=8.9 Hz, J=2.1 Hz, 2H), 7.36 (d, J=7.8 Hz, 2H), 7.44 (d, J=8.9 Hz, 2H), 7.49–7.52 (m, 4H). MS: 600, 338, 300, 280, 232, 204, 122.

EXAMPLE 10

Synthesis of 1,4-Bis(N-3',4'-methylenedioxyphenyl-N-phenylamino)benzene (Exemplified Compound 25; Ar$^1$=Ar$^2$=phenyl, Ar$^3$=p-phenylene)

(1) Synthesis of N-3,4-Methylenedioxyphenyl-N-phenylamine

A mixture of 90 g (0.448 mol) of 3,4-bromomethylenedioxybenzene, 50 g (0.37 mol) of acetanilide, 12 g (0.075 mol) of copper sulfate, and 80 g (0.579 mol) of potassium carbonate was reacted in the same manner as in Example 5 (2) to obtain a crude reaction product. A mixture of this crude product, 121.4 g (1.84 mol)

of 85% KOH, and 200 ml of methanol was refluxed overnight and then concentrated. Water was added thereto. The resultant mixture was extracted with toluene twice. The toluene phase was washed with water three times, dried, and then concentrated. The residue was distilled under vacuum to obtain 65.91 g of N-3,4-methylenedioxyphenyl-N-phenylamine.

Yield, 83.5% (based on acetanilide); bp, 148–150° C./1 mmHg. $^1$H-NMR ($\delta$; ppm in CDCl$_3$): 4.79 (brs, 1H), 5.35 (s, 2H) 6.30 (dd, J=8.3 Hz, J=2.3 Hz, 1H), 6.52 (d, J=2.2 Hz, 1H), 6.58 (d, J=8.3 Hz, 1H), 6.74 (m, 2H), 6.78 (m, 1H), 7.08 (m, 1H). MS: 213, 184, 154.

(2) Synthesis of 1,4-Bis(N-3',4'-methylenedioxyphenyl-N-phenylamino)benzene (Exemplified Compound 25)

A mixture of 7.5 g (35.2 mmol) of N-3,4-methylenedioxyphonyl-N-phenylamine, 5.0 g (15.2 mmol) of 1,4-diiodobenzene, 190 mg (3.0 mmol) of a copper powder, 4.5 g (32.6 mmol) of potassium carbonate, and 100 ml of isobutylbenzene was refluxed for 12 hours with dehydration. The reaction mixture was cooled to about 100° C. and then filtered through a Celite. The Celite was rinsed with 100 ml of toluene and the filtrate was concentrated. To the resultant oily substance was added ethyl acetate/methanol (15 ml/15 ml). This mixture was stirred overnight to precipitate crystals. The crystals obtained were take out by filtration, dissolved in toluene, and purified by silica gel column chromatography (solvent: toluene) to obtain 4.80 g of crystals. These crystals were recrystallized from hexane/toluene (10 ml/10 ml). As a result, 3.80 g of crystals of Exemplified Compound 25 were obtained.

Yield, 49.9%; mp, 169–170° C. $^1$H-NMR ($\delta$; ppm in C$_6$D$_6$): 5.28 (s, 4H), 6.50–6.57 (m, 4H) 6.75 (s, 2H), 6.78–6.83 (m, 2H), 6.96 (s, 4H), 7.02–7.11 (m, 8H). MS: 500, 250, 230, 182, 154, 91.

EXAMPLE 11

Synthesis of 1,4-Bis(N-3',4'-methylenedioxyphenyl-N-m-tolylamino)benzene (Exemplified Compound 27; Ar$^1$=Ar$^2$= m-tolyl, Ar$^3$=p-phenylene)

(1) Synthesis of N-(3,4-Methylenedioxyphenyl-N-m-tolyl) amine

A mixture of 40.0 g (268.1 mol) of m-acetotoluidine, 45.0 g (223.9 mol) of 3,4-bromomethylenedioxybenzene, 8 g (50.1 mol) of copper sulfate, and 31 g (267.7 mmol) of potassium carbonate was reacted in the same manner as in Example 5 (2) to obtain a crude reaction product. A mixture of this crude product, 50 g (757.4 mmol) of 85% KOH, and 200 ml of methanol was refluxed overnight and then concentrated. Water was added thereto. The resultant mixture was extracted with toluene twice. The toluene phase was washed with water three times, dried, and then concentrated. The residue was distilled under vacuum to obtain 24.51 g of N-3,4-methylenedioxyphenyl-N-m-tolylamine.

Yield, 48.2% (based on 3,4-bromomethylenedioxybenzene); bp, 168–175° C./1 mmHg.

(2) Synthesis of 1,4-Bis(N-3',4'-methylenedioxyphenyl-N-m-tolylamino)benzene (Exemplified Compound 27)

A mixture of 8.0 g (35.2 mmol) of N-3,4-methylenedioxyphenyl-N-m-tolylamine, 5.0 g (15.2 mmol) of 1,4-diiodobenzene, 190 mg (3.0 mmol) of a copper powder, 4.5 g (32.6 mmol) of potassium carbonate, and 100 ml of isobutylbenzene was refluxed for 15 hours with dehydration. The resultant reaction mixture was treated in the same manner as in the synthesis of Exemplified Compound 25. As a result, 3.91 g of crystals of Exemplified Compound 27 were obtained.

Yield, 48.7%; mp, 176–176.5° C. $^1$H-NMR ($\delta$; ppm in C$_6$D$_6$): 2.01 (s, 6H), 5.27 (s, 4H) 6.50–6.70 (m, 6H), 6.75–6.82 (m, 2H), 6.93–7.08 (m, 10H). MS: 528, 302, 264, 244, 196, 168.

EXAMPLE 12

Synthesis of 1,4-Bis(N-3',4'-methylenedioxyphenyl-N-4''-ethylphenylamino)benzene (Exemplified Compound 28; Ar$^1$=Ar$^2$=p-ethylphenyl, Ar$^3$=p-phenylene)

A mixture of 8.5 g (35.2 mmol) of 4-ethyl-3',4'-methylenedioxydiphenylamine, 5.0 g (15.2 mmol) of 1,4-diiodobenzene, 190 mg (3.0 mmol) of a copper powder, 4.5 g (32.6 mmol) of potassium carbonate, and 100 ml of isobutylbenzene was refluxed for 8 hours with dehydration. The resultant reaction mixture was treated in the same manner as in the synthesis of Exemplified Compound 25. As a result, 4.22 g of crystals of Exemplified Compound 28 were obtained.

Yield, 49.9%; mp, 196–197.5° C. $^1$H-NMR ($\delta$; ppm in C$_6$D$_6$): 0.68 (t, J=7.6 Hz, 6H), 2.01 (q, J=7.8 Hz, 4H), 4.87 (s, 4H), 6.14 (s, 2H), 6.16 (d, J=2.2 Hz, 2H), 6.40 (d, J=2.0 Hz, 2H), 6.53 (d, J=8.6 Hz, 4H), 6.60 (s, 4H), 6.71 (d, J=8.6 Hz, 4H). MS: 556, 316, 278.

APPLICATION EXAMPLES 1 TO 5

On a thin aluminum film formed on a polyester film by vapor deposition, oxotitanium phthalocyanine (TiOPc) was vapor-deposited at 10$^{-6}$ Torr in a thickness of about 0.8 $\mu$m to form a charge-generating layer. One part by weight of each of Exemplified Compounds 1, 2, 5, 17, and 21 was mixed with 1 part by weight of a POLYCARBONATE resin represented by structural formula (A-2) (POLYCARBONATE Z-200, manufactured by Mitsubishi Gas Chemical Company, Inc.) in 8 parts by weight of dichloroethane to dissolve the solid ingredients. This solution was applied on the charge-generating layer with a doctor blade and dried at 80° C. for 3 hours. Thus, photoreceptors were produced. The electrophotographic photoreceptors thus obtained were statically examined for electrophotographic properties with electrostatic recording paper tester Type EPA-8200 (manufactured by Kawaguchi Denki Seisakusho) as follows. Each photoreceptor was electrostatically charged by –6 kV corona discharge to measure the resultant surface potential V$_0$ (unit: –V). The charged photoreceptor was placed in the dark for 5 seconds [surface potential V$_i$ (unit: –V)], and then irradiated with light from a halogen lamp at an illuminance of 5 lx to determine the exposure required for the surface potential V$_i$ to decrease by half, i.e., half-decay exposure E$_{1/2}$ (lx·sec), and the exposure required for the surface potential to decrease to one sixth, E$_{1/6}$. Subsequently, the photoreceptor was irradiated for 10 seconds with light at an illuminance of 5 lx, and the residual surface potential V$_{R10}$ (–V) was determined. The results obtained are shown in Table 2.

COMPARATIVE EXAMPLE 1

Oxotitanium phthalocyanine (TiOPc) was vapor-deposited in the same manner as in Application Example 1 to form a charge-generating layer. One part by weight of Comparative Compound 1, represented by the following structural formula, was mixed with 1 part by weight of a polycarbonate resin represented by structural formula (A-2) (POLYCARBONATE Z-200, manufactured by Mitsubishi Gas Chemical Company Inc.) in 8 parts by weight of dichloroethane to dissolve the solid ingredients. This solution was applied on the charge-generating layer and dried in the same manner as in Application Example 1 to produce a photoreceptor. This photoreceptor was evaluated for electrophotographic properties. The results obtained are shown in Table 2.

Table 2 shows that the electrophotographic photoreceptors each employing a compound of the present invention had better sensitivity (smaller values of $E_{1/2}$ and $E_{1/6}$) and a lower residual potential than the photoreceptor employing Comparative Compound 1.

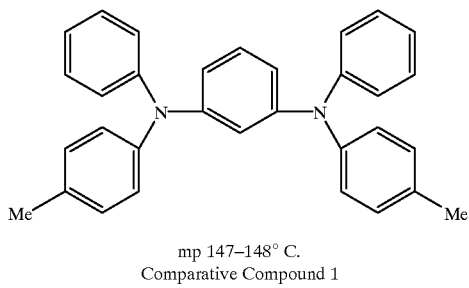

mp 147–148° C.
Comparative Compound 1 weight of each of Comparative Compound 1 and Comparative Compound 2, represented by the following structural formula, was mixed with 1 part by weight of a polycarbonate resin represented by structural formula (A-2) (POLYCARBONATE Z-200, manufactured by Mitsubishi Gas Chemical Company, Inc.) or a bisphenol A/biphenol type copolycarbonate resin represented by structural formula (B-1) (TOUGH Z-300, manufactured by Idemitsu Kosan Co., Ltd.) in 8 parts by weight of dichloroethane to dissolve the solid ingredients. This solution was applied on the charge-generating layer and dried in the same manner as in Application Example 6. Thus, photoreceptors were produced. The electrophotographic properties thereof were evaluated, and the results obtained are shown in Table 3. It was attempt to dissolve Comparative Compound 3, represented by the following structural formula, by mixing 1 part by weight of the compound with 1 part by weight of the

TABLE 2

| | Charge-transporting material | Polymeric binder | Charge-generating material | $V_0$ (-V) | $V_i$ (-V) | $V_{R10}$ (-V) | $E_½$ (lx · s) | $E_⅙$ (lx · s) |
|---|---|---|---|---|---|---|---|---|
| Application Example 1 | Exemplified Compound 1 (1 pt. wt.) | Pc (A-2) (1 pt. wt.) | vapor-deposited TiOPc | 930 | 742 | 2 | 0.59 | 1.34 |
| Application Example 2 | Exemplified Compound 2 (1 pt. wt.) | Pc (A-2) (1 pt. wt.) | vapor-deposited TiOPc | 824 | 608 | 1 | 0.57 | 1.27 |
| Application Example 3 | Exemplified Compound 5 (1 pt. wt.) | Pc (A-2) (1 pt. wt.) | vapor-deposited TiOPc | 991 | 717 | 2 | 0.54 | 1.26 |
| Application Example 4 | Exemplified Compound 17 (1 pt. wt.) | PC (A-2) (1 pt. wt.) | vapor-deposited TiOPc | 652 | 493 | 20 | 0.73 | 2.66 |
| Application Example 5 | Exemplified Compound 21 (1 pt. wt.) | Pc (A-2) (1 pt. wt.) | vapor-deposited TiOPc | 473 | 311 | 24 | 0.78 | 5.12 |
| Comparative Example 1 | Comparative Compound 1 (1 pt. wt.) | Pc (A-2) (1 pt. wt.) | vapor-deposited TiOPc | 996 | 850 | 130 | 1.20 | 5.50 |

APPLICATION EXAMPLES 6 TO 13

One part by weight of chlorodian blue (CDB) was kneaded together with 1 part by weight of a polycarbonate resin (YUPILON E-2000, manufactured by Mitsubishi Gas Chemical Company, Inc.) in a ball mill for 5 hours using 30 parts by weight of dichloroethane as a solvent. The pigment dispersion obtained was applied with a wire-wound bar on a sheet obtained by vapor-depositing aluminum on a poly (ethylene terephthalate) (PET) film, and the coating was dried at 45° C. for 3 hours to form a charge-generating layer having a thickness of about 1 μm.

One part by weight of each of Exemplified Compounds 1, 2, 5, 17, 19, 21, and 25 was mixed with 1 part by weight of a polycarbonate resin represented by structural formula (A-2) (POLYCARBONATE Z, manufactured by Mitsubishi Gas Chemical Company, Inc.) or a bisphenol A/biphenol type copolycarbonate resin represented by structural formula (B-1) (TOUGH Z-300, manufactured by Idemitsu Kosan Co., Ltd.) in 8 parts by weight of dichloroethane to dissolve the solid ingredients. This solution was applied on the charge-generating layer with a doctor blade and dried at 80° C. for 3 hours. Thus, photoreceptors were produced. The electrophotographic properties thereof were evaluated in the same manner as in Application Example 1. The results obtained are shown in Table 3.

COMPARATIVE EXAMPLES 2 TO 4

CDB was used to form a charge-generating layer in the same manner as in Application Example 6. One part by polycarbonate resin represented by structural formula (A-2) (POLYCARBONATE Z, manufactured by Mitsubishi Gas Chemical Company, Inc.) in 8 parts by weight of dichloroethane. However, Comparative Compound 3 did not dissolve.

Table 3 shows that the electrophotographic photoreceptors each employing a compound of the present invention had better sensitivity (smaller values of $E_{1/2}$ and $E_{1/6}$) and a lower residual potential than the photoreceptors respectively employing Comparative Compounds 1 and 2. The photoreceptor of Comparative Example 3 had so poor sensitivity that the value of $E_{1/6}$ thereof was unable to be measured.

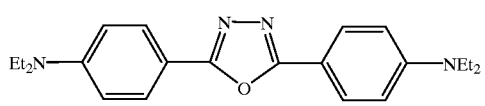

mp 147–148° C.
Comparative Compound 2

-continued

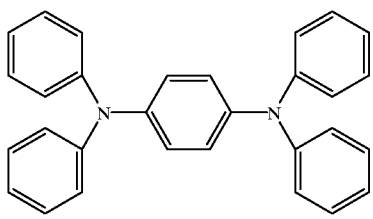

mp 202–204° C.
Comparative Compound 3 type copolycarbonate resin represented by structural formula (B-1) (TOUGH Z-300, manufactured by Idemitsu Kosan Co., Ltd.) in 8 parts by weight of dichloroethane to dissolve the solid ingredients. This solution was applied on the charge-generating layer with a doctor blade and dried at 80° C. for 3 hours. Thus, photoreceptors were produced. The electrophotographic properties of the photoreceptors obtained were examined in the same manner as in Application Example 1. The results obtained are shown in Table 4.

COMPARATIVE EXAMPLE 5

Crystalline TiOPc (1) was used to form a charge-generating layer in the same manner as in Application Example 14. One part by weight of Comparative Compound

TABLE 3

|  | Charge-transporting material | Polymeric binder | Charge-generating material | $V_0$ (−V) | $V_i$ (−V) | $V_{R10}$ (−V) | $E_½$ (lx · s) | $E_⅙$ (lx · s) |
|---|---|---|---|---|---|---|---|---|
| Application Example 6 | Exemplified Compound 1 (1 pt. wt.) | Pc (A-2) (1 pt. wt.) | CDB | 951 | 823 | 12 | 3.04 | 6.61 |
| Application Example 7 | Exemplified Compound 2 (1 pt. wt.) | Pc (A-2) (1 pt. wt.) | CDB | 934 | 680 | 5 | 2.19 | 4.75 |
| Application Example 8 | Exemplified Compound 5 (1 pt. wt.) | Pc (A-2) (1 pt. wt.) | CDB | 1394 | 1198 | 21 | 3.17 | 6.70 |
| Application Example 9 | Exemplified Compound 17 (1 pt. wt.) | Pc (A-2) (1 pt. wt.) | CDB | 978 | 878 | 15 | 6.36 | 15.93 |
| Application Example 10 | Exemplified Compound 19 (1 pt. wt.) | Pc (A-2) (1 pt. wt.) | CDB | 1093 | 976 | 20 | 6.65 | 16.82 |
| Application Example 11 | Exemplified Compound 21 (1 pt. wt.) | Pc (A-2) (1 pt. wt.) | CDB | 828 | 732 | 4 | 7.01 | 18.70 |
| Application Example 12 | Exemplified Compound 21 (1 pt. wt.) | Pc (B-1) (1 pt. wt.) | CDB | 1045 | 961 | 11 | 7.00 | 19.05 |
| Application Example 13 | Exemplified Compound 25 (1 pt. wt.) | Pc (A-2) (1 pt. wt.) | CDB | 752 | 551 | 2 | 2.32 | 4.76 |
| Comparative Example 2 | Comparative Compound 1 (1 pt. wt.) | Pc (A-2) (1 pt. wt.) | CDB | 1030 | 970 | 60 | 7.60 | 19.50 |
| Comparative Example 3 | Comparative Compound 2 (1 pt. wt.) | Pc (B-1) (1 pt. wt.) | CDB | 1106 | 1005 | 328 | 26.60 | unable to be measured |
| Comparative Example 4 | Comparative Compound 3 (1 pt. wt.) | Pc (A-2) (1 pt. wt.) | unable to be measured because dissolution in the binder solution was impossible | | | | | |

APPLICATION EXAMPLES 14 TO 16

According to a method described in JP-A-1-291256, 40 parts by weight of crystalline oxytitanium phthalocyanine (crystalline TiOPc (1)) was added to a binder resin solution obtained by dissolving 35 parts by weight of a butyral resin (POLY(VINYL BUTYRAL) BL-1, manufactured by Sekisui Chemical Co., Ltd.) in 1,425 parts by weight of tetrahydrofuran, and the pigment was dispersed by treating the mixture with an oscillating mill for 2 hours together with glass beads. This dispersion was applied with a wire-wound bar on a sheet obtained by vapor-depositing aluminum on a poly(ethylene terephthalate) (PET) film, and the coating was dried to form a charge-generating layer.

One part by weight of each of Exemplified Compounds 1, 5, and 17 was mixed with 1 part by weight of a polycarbonate resin represented by structural formula (A-2) (POLYCARBONATE Z-200, manufactured by Mitsubishi Gas Chemical Company, Inc.) or a bisphenol A/biphenol 4, represented by the following structural formula, was mixed with 1 part by weight of a bisphenol A/biphenol type copolycarbonate resin represented by structural formula (B-1) (TOUGH Z-300, manufactured by Idemitsu Kosan Co., Ltd.) in 8 parts by weight of dichloroethane to dissolve the solid ingredients. This solution was applied on the charge-generating layer and dried in the same manner as in Application Example 14 to produce a photoreceptor. The electrophotographic properties thereof were evaluated, and the results obtained are shown in Table 4.

Table 4 shows that the electrophotographic photoreceptors each employing a compound of the present invention had better sensitivity (smaller values of $E_{1/2}$ and $E_{1/6}$) and a lower residual potential than the photoreceptor employing Comparative Compound 4.

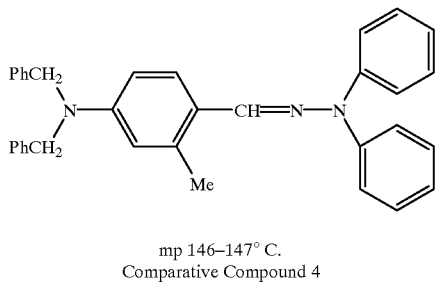

mp 146–147° C.
Comparative Compound 4 receptors were produced. The electrophotographic properties of these photoreceptors were evaluated in the same manner as in Application Example 1. The results obtained are shown in Table 5.

COMPARATIVE EXAMPLES 6 AND 7

τ-Form metal-free phthalocyanine (τ-$H_2$Pc) was used to form a charge-generating layer in the same manner as in Application Example 17. One part by weight of Comparative Compound 2 was mixed with 1 part by weight of a bisphenol A/biphenol type copolycarbonate resin represented by structural formula (B-1) (TOUGH Z-300, manufactured by Idemitsu Kosan Co., Ltd.) in 8 parts by weight of dichloroethane to dissolve the solid ingredients. This

TABLE 4

| | Charge-transporting material | Polymeric binder | Charge generating material | $V_0$ (-V) | $V_i$ (-V) | $V_{R10}$ (-V) | $E_{½}$ (lx · s) | $E_{⅙}$ (lx · s) |
|---|---|---|---|---|---|---|---|---|
| Application Example 14 | Exemplified Compound 1 (1 pt. wt.) | Pc (A-2) (1 pt. wt.) | crystalline TiOPc (1) | 879 | 599 | 13 | 0.46 | 0.84 |
| Application Example 15 | Exemplified Compound 5 (1 pt. wt.) | Pc (A-2) (1 pt. wt.) | crystalline TiOPc (1) | 698 | 397 | 17 | 0.38 | 0.70 |
| Application Example 16 | Exemplified Compound 17 (1 pt. wt.) | Pc (B-1) (1 pt. wt.) | crystalline TiOPc (1) | 684 | 393 | 8 | 0.30 | 1.31 |
| Comparative Example 5 | Comparative Compound 4 (1 pt. wt.) | Pc (B-1) (1 pt. wt.) | crystalline TiOPc (1) | 921 | 702 | 21 | 0.52 | 1.35 |

APPLICATION EXAMPLES 17 TO 24

One part by weight of τ-form metal-free phthalocyanine (τ-$H_2$Pc) was kneaded together with 1 part by weight of a butyral resin (POLY(VINYL BUTYRAL) BL-1, manufactured by Sekisui Chemical Co., Ltd.) in a ball mill for 5 hours using 30 parts by weight of tetrahydrofuran as a solvent. The pigment dispersion obtained was applied on a sheet obtained by vapor-depositing aluminum on a poly (ethylene terephthalate) (PET) film, and the coating was dried at 50° C. for 2 hours. One part by weight of each of Exemplified Compounds 1, 5, 17, 19, 21, and 25 was mixed with 1 part by weight of a polycarbonate resin represented by structural formula (A-2) (POLYCARBONATE Z-200, manufactured by Mitsubishi Gas Chemical Company, Inc.) or a bisphenol A/biphenol type copolycarbonate resin represented by structural formula (B-1) (TOUGH Z-300, manufactured by Idemitsu Kosan Co., Ltd.) in 8 parts by weight of dichloroethane to dissolve the solid ingredients. This solution was applied on the charge-generating layer with a doctor blade and dried at 80° C. for 3 hours. Thus, photosolution was applied on the charge-generating layer and dried in the same manner as in Application Example 17. Thus, photoreceptors were produced. The electrophotographic properties thereof were evaluated, and the results obtained are shown in Table 5. It was attempt to dissolve Comparative Compound 3 by mixing 1 part by weight of the compound with 1 part by weight of the polycarbonate resin represented by structural formula (A-2) (POLYCARBONATE Z-200, manufactured by Mitsubishi Gas Chemical Company, Inc.) in 8 parts by weight of dichloroethane. However, Comparative Compound 3 did not dissolve.

Table 5 shows that the electrophotographic photoreceptors each employing a compound of the present invention had better sensitivity (smaller values of $E_{1/2}$ and $E_{1/6}$) and a lower residual potential than the photoreceptor employing Comparative Compound 2.

TABLE 5

| | Charge-transporting material | Polymeric binder | Charge-generating material | $V_0$ (-V) | $V_i$ (-V) | $V_{R10}$ (-V) | $E_{½}$ (lx · s) | $E_{⅙}$ (lx · s) |
|---|---|---|---|---|---|---|---|---|
| Application Example 17 | Exemplified Compound 1 (1 pt. wt.) | Pc (A-2) (1 pt. wt.) | τ-$H_2$Pc | 1083 | 916 | 15 | 0.75 | 1.39 |
| Application Example 18 | Exemplified Compound 5 (1 pt. wt.) | Pc (A-2) (1 pt. wt.) | τ-$H_2$Pc | 1028 | 896 | 10 | 0.76 | 1.39 |
| Application Example 19 | Exemplified Compound 17 (1 pt. wt.) | Pc (A-2) (1 pt. wt.) | τ-$H_2$Pc | 1000 | 871 | 11 | 0.69 | 1.42 |

TABLE 5-continued

| | Charge-transporting material | Polymeric binder | Charge-generating material | $V_0$ (-V) | $V_i$ (-V) | $V_{R10}$ (-V) | $E_{½}$ (lx · s) | $E_{⅙}$ (lx · s) |
|---|---|---|---|---|---|---|---|---|
| Application Example 20 | Exemplified Compound 17 (1 pt. wt.) | Pc (B-1) (1 pt. wt.) | τ-H$_2$Pc | 1008 | 853 | 7 | 0.67 | 1.34 |
| Application Example 21 | Exemplified Compound 19 (1 pt. wt.) | Pc (A-2) (1 pt. wt.) | τ-H$_2$Pc | 1104 | 946 | 12 | 0.66 | 1.36 |
| Application Example 22 | Exemplified Compound 19 (1 pt. wt.) | Pc (B-1) (1 pt. wt.) | τ-H$_2$Pc | 1040 | 915 | 5 | 0.73 | 1.44 |
| Application Example 23 | Exemplified Compound 21 (1 pt. wt.) | Pc (A-2) (1 pt. wt.) | τ-H$_2$Pc | 972 | 863 | 17 | 0.78 | 1.54 |
| Application Example 24 | Exemplified Compound 25 (1 pt. wt.) | Pc (A-2) (1 pt. wt.) | τ-H$_2$Pc | 889 | 655 | 4 | 0.74 | 1.36 |
| Comparative Example 6 | Comparative Compound 2 (1 pt. wt.) | Pc (B-1) (1 pt. wt.) | τ-H$_2$Pc | 1042 | 923 | 89 | 1.07 | 5.13 |
| Comparative Example 7 | Comparative Compound 3 (1 pt. wt.) | Pc (A-2) (1 pt. wt.) | unable to be measured because dissolution in the binder solution was impossible | | | | | |

APPLICATION EXAMPLES 25 TO 32

One part by weight of x-form metal-free phthalocyanine (x-H$_2$Pc) was kneaded together with 1 part by weight of a butyral resin (POLY(VINYL BUTYRAL) BL-1, manufactured by Sekisui Chemical Co., Ltd.) in a ball mill for 5 hours using 30 parts by weight of tetrahydrofuran as a solvent. The pigment dispersion obtained was applied on a sheet obtained by vapor-depositing aluminum on a poly (ethylene terephthalate) (PET) film, and the coating was dried at 50° C. for 2 hours. One part by weight of each of Exemplified Compounds 1, 5, 17, 19, 21, and 25 was mixed with 1 part by weight of a polycarbonate resin represented by structural formula (A-2) (POLYCARBONATE Z-200, manufactured by Mitsubishi Gas Chemical Company, Inc.) or a bisphenol A/biphenol type copolycarbonate resin represented by structural formula (B-1) (TOUGH Z-300, manufactured by Idemitsu Kosan Co., Ltd.) in 8 parts by weight of dichloroethane to dissolve the solid ingredients. This solution was applied on the charge-generating layer with a doctor blade and dried at 80° C. for 3 hours. Thus, photoreceptors were produced. The photoreceptors obtained were examined for electrophotographic properties in the same manner as in Application Example 1. The results obtained are shown in Table 6.

COMPARATIVE EXAMPLES 8 TO 10 x-Form metal-free phthalocyanine (x-H$_2$Pc) was used to form a charge-generating layer in the same manner as in Application Example 25. One part by weight of each of Comparative Compounds 2 and 4 was mixed with 1 part by weight of a bisphenol A/biphenol type copolycarbonate resin represented by structural formula (B-1) (TOUGH Z-300, manufactured by Idemitsu Kosan Co., Ltd.) in 8 parts by weight of dichloroethane to dissolve the solid ingredients. This solution was applied on the charge-generating layer and dried in the same manner as in Application Example 25. Thus, photoreceptors were produced. The electrophotographic properties thereof were evaluated, and the results obtained are shown in Table 6. It was attempt to dissolve Comparative Compound 3 by mixing 1 part by weight of the compound with 1 part by weight of the polycarbonate resin represented by structural formula (A-2) (POLYCARBONATE Z, manufactured by Mitsubishi Gas Chemical Company, Inc.) in 8 parts by weight of dichloroethane. However, Comparative Compound 3 did not dissolve.

Table 6 shows that the electrophotographic photoreceptors each employing a compound of the present invention had better sensitivity (smaller values of $E_{1/2}$ and $E_{1/6}$) and a lower residual potential than the photoreceptors respectively employing Comparative Compounds 2 and 4.

TABLE 6

| | Charge-transporting material | Polymeric binder | Charge-generating material | $V_0$ (-V) | $V_i$ (-V) | $V_{R10}$ (-V) | $E_{½}$ (lx · s) | $E_{⅙}$ (lx · s) |
|---|---|---|---|---|---|---|---|---|
| Application Example 25 | Exemplified Compound 1 (1 pt. wt.) | Pc (A-2) (1 pt. wt.) | x-H$_2$Pc | 1036 | 937 | 11 | 0.96 | 1.88 |
| Application Example 26 | Exemplified Compound 5 (1 pt. wt.) | Pc (A-2) (1 pt. wt.) | x-H$_2$Pc | 947 | 821 | 10 | 0.92 | 1.72 |
| Application Example 27 | Exemplified Compound 17 (1 pt. wt.) | Pc (A-2) (1 pt. wt.) | x-H$_2$Pc | 1016 | 904 | 16 | 0.87 | 1.86 |

TABLE 6-continued

| | Charge-transporting material | Polymeric binder | Charge-generating material | $V_0$ (-V) | $V_i$ (-V) | $V_{R10}$ (-V) | $E_{1/2}$ (lx·s) | $E_{1/6}$ (lx·s) |
|---|---|---|---|---|---|---|---|---|
| Application Example 28 | Exemplified Compound 17 (1 pt. wt.) | Pc (B-1) (1 pt. wt.) | x-H$_2$Pc | 955 | 858 | 9 | 0.85 | 1.85 |
| Application Example 29 | Exemplified Compound 19 (1 pt. wt.) | Pc (A-2) (1 pt. wt.) | x-H$_2$Pc | 1193 | 1071 | 13 | 0.86 | 1.88 |
| Application Example 30 | Exemplified Compound 21 (1 pt. wt.) | Pc (A-2) (1 pt. wt.) | x-H$_2$Pc | 888 | 823 | 6 | 0.98 | 2.12 |
| Application Example 31 | Exemplified Compound 21 (1 pt. wt.) | Pc (B-1) (1 pt. wt.) | x-H$_2$Pc | 887 | 796 | 0 | 0.85 | 1.78 |
| Application Example 32 | Exemplified Compound 25 (1 pt. wt.) | Pc (A-2) (1 pt. wt.) | x-H$_2$Pc | 1072 | 952 | 1 | 0.96 | 1.94 |
| Comparative Example 8 | Comparative Compound 2 (1 pt. wt.) | Pc (B-1) (1 pt. wt.) | x-H$_2$Pc | 953 | 851 | 51 | 1.11 | 5.39 |
| Comparative Example 9 | Comparative Compound 3 (1 pt. wt.) | Pc (A-2) (1 pt. wt.) | unable to be measured because dissolution in the binder solution was impossible | | | | | |
| Comparative Example 10 | Comparative Compound 4 (1 pt.wt.) | Pc (B-1) (1 pt. wt.) | x-H$_2$Pc | 1066 | 944 | 27 | 1.34 | 3.27 |

APPLICATION EXAMPLES 33 TO 39

One part by weight of the bisazo pigment represented by the following structural formula (K) was kneaded together with 1 part by weight of a polycarbonate resin (YUPILON E-2000, manufactured by Mitsubishi Gas Chemical Company, Inc.) in a ball mill for 5 hours using 30 parts by weight of dichloroethane as a solvent. The pigment dispersion obtained was applied with a wire-wound bar on a sheet obtained by vapor-depositing aluminum on a poly(ethylene terephthalate) (PET) film, and the coating was dried at 45° C. for 3 hours to form a charge-generating layer having a thickness of about 1 μm. One part by weight of each of Exemplified Compounds 1, 5, 17, 19, and 21 was mixed with 1 part by weight of a polycarbonate resin represented by structural formula (A-2) (POLYCARBONATE Z-200, manufactured by Mitsubishi Gas Chemical Company, Inc.) or a bisphenol A/biphenol type copolycarbonate resin represented by structural formula (B-1) (TOUGH Z-300, manufactured by Idemitsu Kosan Co., Ltd.) in 8 parts by weight of dichloroethane to dissolve the solid ingredients. This solution was applied on the charge-generating layer with a doctor blade and dried at 80° C. for 3 hours. Thus, photoreceptors were produced. The photoreceptors obtained were examined for electrophotographic properties in the same manner as in Application Example 1. The results obtained are shown in Table 7.

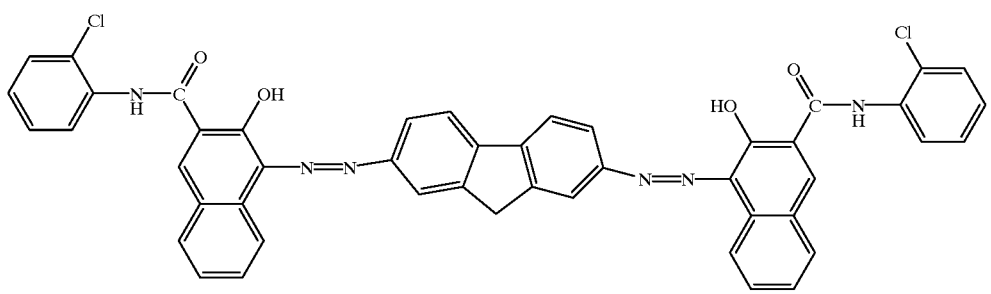

(K)

Bisazo

COMPARATIVE EXAMPLES 11 AND 12

The bisazo pigment represented by structural formula (K) was used to form a charge-generating layer in the same manner as in Application Example 33. One part by weight of each of Comparative Compound 2 and Comparative Compound 5 (the same compound as that represented by formula (4)) was mixed with 1 part by weight of a polycarbonate resin represented by structural formula (A-2) (POLYCARBONATE Z-200, manufactured by Mitsubishi Gas Chemical Company, Inc.) or a bisphenol A/biphenol type copolycarbonate resin represented by structural formula (B-1) (TOUGH Z-300, manufactured by Idemitsu Kosan Co., Ltd.) in 8 parts by weight of dichloroethane to dissolve the solid ingredients. This solution was applied on the charge-generating layer and dried in the same manner as in Application Example 33. Thus, photoreceptors were produced. The electrophotographic properties thereof were evaluated, and the results obtained are shown in Table 7.

Table 7 shows that the electrophotographic photoreceptors each employing a compound of the present invention had better sensitivity (smaller values of $E_{1/2}$ and $E_{1/6}$) and a lower residual potential than the photoreceptors respectively employing Comparative Compounds 2 and 5.

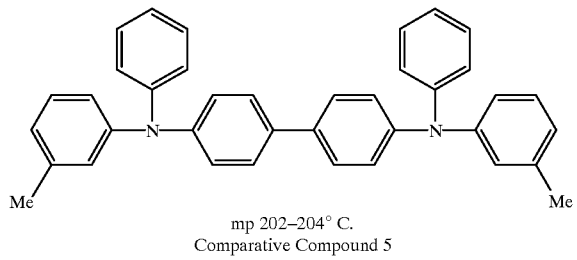

mp 202–204° C.
Comparative Compound 5

(the compound represented by formula (4))

Kosan Co., Ltd.) in 8 parts by weight of dichloroethane to dissolve the solid ingredients. This solution was applied on the charge-generating layer with a doctor blade and dried at 80° C. for 3 hours. Thus, photoreceptors were produced. The photoreceptors obtained were examined for electrophotographic properties in the same manner as in Application Example 1. The results obtained are shown in Table 8.

COMPARATIVE EXAMPLES 13 TO 15

Crystalline TiOPc (2) was used to form a charge-generating layer in the same manner as in Application Example 40. One part by weight of each of Comparative Compounds 2 and 4 was mixed with 1 part by weight of a bisphenol A/biphenol type copolycarbonate resin represented by structural formula (B-1) (TOUGH Z-300, manufactured by Idemitsu Kosan Co., Ltd.) in 8 parts by weight of dichloroethane to dissolve the solid ingredients. This solution was applied on the charge-generating layer and dried in the same manner as in Application Example 40. Thus, photoreceptors were produced. The electrophoto-

TABLE 7

| | Charge-transporting material | Polymeric binder | Charge-generating material | $V_0$ (−V) | $V_i$ (−V) | $V_{R10}$ (−V) | $E_{1/2}$ (lx · s) | $E_{1/6}$ (lx · s) |
|---|---|---|---|---|---|---|---|---|
| Application Example 33 | Exemplified Compound 1 (1 pt. wt.) | Pc (A-2) (1 pt. wt.) | bisazo (K) | 670 | 457 | 13 | 3.46 | 6.52 |
| Application Example 34 | Exemplified Compound 5 (1 pt. wt.) | Pc (A-2) (1 pt. wt.) | bisazo (K) | 594 | 342 | 10 | 2.87 | 5.06 |
| Application Example 35 | Exemplified Compound 17 (1 pt. wt.) | Pc (A-2) (1 pt. wt.) | bisazo (K) | 705 | 569 | 1 | 2.21 | 4.36 |
| Application Example 36 | Exemplified Comound 17 (1 pt. wt.) | Pc (B-1) (1 pt. wt.) | bisazo (K) | 702 | 557 | 3 | 2.26 | 4.14 |
| Application Example 37 | Exemplified Compound 19 (1 pt. wt.) | Pc (A-2) (1 pt. wt.) | bisazo (K) | 882 | 752 | 6 | 2.36 | 4.67 |
| Application Example 38 | Exemplified Compound 21 (1 pt. wt.) | Pc (A-2) (1 pt. wt.) | bisazo (K) | 802 | 643 | 1 | 3.13 | 6.06 |
| Application Example 39 | Exemplified Compound 21 (1 pt. wt.) | Pc (B-1) (1 pt. wt.) | bisazo (K) | 846 | 678 | 4 | 2.58 | 4.88 |
| Comparative Example 11 | Comparative Compound 2 (1 pt. wt.) | Pc (B-1) (1 pt. wt.) | bisazo (K) | 977 | 851 | 54 | 3.47 | 9.30 |
| Comparative Example 12 | Comparative Compound 5 (1 pt. wt.) | Pc (A-2) (1 pt. wt.) | bisazo (K) | 784 | 561 | 3 | 5.24 | 9.37 |

APPLICATION EXAMPLES 40 TO 47

Figure 2:
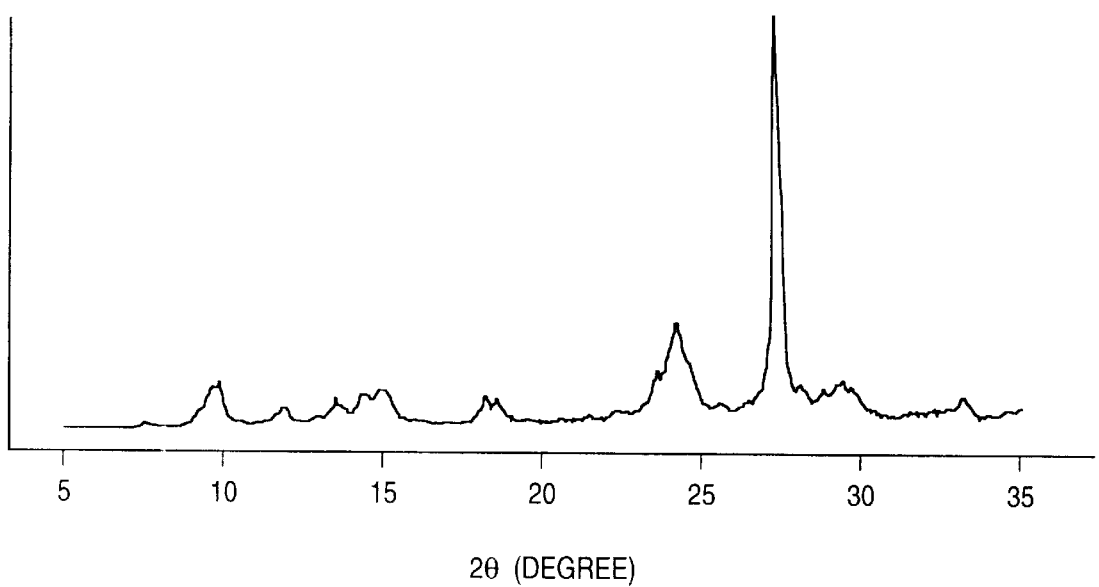
FIG. 2 is an X-ray diffraction curve of a crystalline oxytitanyl phthalocyanine.

A charge-generating layer was formed in the same manner as in Application Example 14, except that the crystalline oxytitanium phthalocyanine manufactured by Zeneka Limited (crystalline TiOPc (2); an X-ray diffraction curve thereof is shown in FIG. 2) was used in place of the crystalline oxytitanium phthalocyanine described in JP-A-1-291256 (crystalline TiOPc (1)). One part by weight of each of Exemplified Compounds 1, 5, 17, 19, 21, and 25 was mixed with 1 part by weight of a polycarbonate resin represented by structural formula (A-2) (POLYCARBONATE Z-200, manufactured by Mitsubishi Gas Chemical Company, Inc.) or a bisphenol A/biphenol type copolycarbonate resin represented by structural formula (B-1) (TOUGH Z-300, manufactured by Idemitsu graphic properties thereof were evaluated, and the results obtained are shown in Table 8. It was attempt to dissolve Comparative Compound 3 by mixing 1 part by weight of the compound with 1 part by weight of the polycarbonate resin represented by structural formula (A-2) (POLYCARBONATE Z, manufactured by Mitsubishi Gas Chemical Company, Inc.) in 8 parts by weight of dichloroethane. However, Comparative Compound 3 did not dissolve.

Table 8 shows that the electrophotographic photoreceptors each employing a compound of the present invention had better sensitivity (smaller values of $E_{1/2}$ and $E_{1/6}$) and a lower residual potential than the photoreceptors respectively employing Comparative Compounds 2 and 4.

TABLE 8

| | Charge-transporting material | Polymeric binder | Charge-generating material | $V_0$ (-V) | $V_i$ (-V) | $V_{R10}$ (-V) | $E_{1/2}$ (lx·s) | $E_{1/6}$ (lx·s) |
|---|---|---|---|---|---|---|---|---|
| Application Example 40 | Exemplified Compound 1 (1 pt. wt.) | Pc (A-2) (1 pt. wt.) | crystalline TiOPc (2) | 633 | 487 | 4 | 0.22 | 0.37 |
| Application Example 41 | Exemplified Compound 5 (1 pt. wt.) | Pc (A-2) (1 pt. wt.) | crystalline TiOPc (2) | 600 | 452 | 4 | 0.24 | 0.40 |
| Application Example 42 | Exemplified Compound 17 (1 pt. wt.) | Pc (A-2) (1 pt. wt.) | crystalline TiOPc (2) | 654 | 526 | 11 | 0.26 | 0.57 |
| Application Example 43 | Exemplified Compound 17 (1 pt. wt.) | Pc (B-1) (1 pt. wt.) | crystalline TiOPc (2) | 704 | 576 | 8 | 0.27 | 0.52 |
| Application Example 44 | Exemplified Compound 19 (1 pt. wt.) | Pc (A-2) (1 pt. wt.) | crystalline TiOPc (2) | 769 | 573 | 11 | 0.23 | 0.82 |
| Application Example 45 | Exemplified Compound 21 (1 pt. wt.) | Pc (A-2) (1 pt. wt.) | crystalline TiOPc (2) | 761 | 624 | 1 | 0.29 | 0.51 |
| Application Example 46 | Exemplified Compound 21 (1 pt. wt.) | Pc (B-1) (1 pt. wt.) | crystalline TiOPc (2) | 729 | 571 | 5 | 0.26 | 0.44 |
| Application Example 47 | Exemplified Compound 25 (1 pt. wt.) | Pc (A-2) (1 pt. wt.) | crystalline TiOPc (2) | 608 | 394 | 1 | 0.33 | 0.71 |
| Comparative Example 13 | Comparative Compound 2 (1 pt. wt.) | Pc (B-1) (1 pt. wt.) | crystalline TiOPc (2) | 938 | 764 | 59 | 0.52 | 5.01 |
| Comparative Example 14 | Comparative Compound 3 (1 pt. wt.) | Pc (A-2) (1 pt. wt.) | unable to be measured because dissolution in the binder solution was impossible | | | | | |
| Comparative Example 15 | Comparative Compound 4 (1 pt. wt.) | Pc (B-1) (1 pt. wt.) | crystalline TiOPc (2) | 774 | 604 | 12 | 0.40 | 0.90 |

APPLICATION EXAMPLES 48 TO 53

The oxytitanium phthalocyanine described in JP-A-2-28265 (crystalline TiOPc (3)) was used together with a polybutyral and THF to prepare a dispersion by the method described in JP-A-2-28265. This dispersion was applied with a wire-wound bar on a sheet obtained by vapor-depositing aluminum on a poly(ethylene terephthalate) (PET) film, and the coating was dried to form a charge-generating layer. One part by weight of each of Exemplified Compounds 17, 19, 21, and 25 was mixed with 1 part by weight of a polycarbonate resin represented by structural formula (A-2) (POLYCARBONATE Z-200, manufactured by Mitsubishi Gas Chemical Company, Inc.) or a bisphenol A/biphenol type copolycarbonate resin represented by structural formula (B-1) (TOUGH Z-300, manufactured by Idemitsu Kosan Co., Ltd.) in 8 parts by weight of dichloroethane to dissolve the solid ingredients. This solution was applied on the charge-generating layer with a doctor blade and dried at 80° C. for 3 hours. Thus, photoreceptors were produced. The photoreceptors obtained were examined for electrophotographic properties in the same manner as in Application Example 1. The results obtained are shown in Table 9.

COMPARATIVE EXAMPLES 16 TO 18

Crystalline TiOPc (3) was used to form a charge-generating layer in the same manner as in Application Example 48. One part by weight of each of Comparative Compounds 2 and 4 was mixed with a bisphenol A/biphenol type copolycarbonate resin represented by structural formula (B-1) (TOUGH Z-300, manufactured by Idemitsu Kosan Co., Ltd.) in 8 parts by weight of dichloroethane to dissolve the solid ingredients. This solution was applied on the charge-generating layer and dried in the same manner as in Application Example 48. Thus, photoreceptors were produced. The electrophotographic properties thereof were evaluated, and the results obtained are shown in Table 9. It was attempt to dissolve Comparative Compound 3 by mixing 1 part by weight of the compound with 1 part by weight of the polycarbonate resin represented by structural formula (A-2) (POLYCARBONATE Z-200, manufactured by Mitsubishi Gas Chemical Company, Inc.) in 8 parts by weight of dichloroethane. However, Comparative Compound 3 did not dissolve.

Table 9 shows that the electrophotographic photoreceptors each employing a compound of the present invention had better sensitivity (smaller values of $E_{1/2}$ and $E_{1/6}$) than the photoreceptors respectively employing Comparative Compounds 2 and 4.

TABLE 9

| | Charge-transporting material | Polymeric binder | Charge-generating material | $V_0$ (-V) | $V_i$ (-V) | $V_{R10}$ (-V) | $E_{1/2}$ (lx·s) | $E_{1/6}$ (lx·s) |
|---|---|---|---|---|---|---|---|---|
| Application Example 48 | Exemplified Compound 17 (1 pt. wt.) | Pc (A-2) (1 pt. wt.) | crystalline TiOPc (3) | 918 | 754 | 25 | 0.28 | 0.54 |

TABLE 9-continued

| | Charge-transporting material | Polymeric binder | Charge-generating material | $V_0$ (-V) | $V_i$ (-V) | $V_{R10}$ (-V) | $E_{½}$ (lx·s) | $E_{⅙}$ (lx·s) |
|---|---|---|---|---|---|---|---|---|
| Application Example 49 | Exemplified Compound 17 (1 pt.wt.) | Pc (B-1) (1 pt. wt.) | crystalline TiOPc (3) | 940 | 783 | 26 | 0.28 | 0.52 |
| Application Example 50 | Exemplified Compound 19 (1 pt. wt.) | Pc (A-2) (1 pt. wt.) | crystalline TiOPc (3) | 946 | 738 | 41 | 0.23 | 0.57 |
| Application Example 51 | Exemplified Compound 21 (1 pt. wt.) | Pc (A-2) (1 pt. wt.) | crystalline TiOPc (3) | 920 | 769 | 39 | 0.31 | 0.62 |
| Application Example 52 | Exemplified Compound 21 (1 pt. wt.) | Pc (B-1) (1 pt. wt.) | crystalline TiOPc (3) | 939 | 761 | 82 | 0.28 | 0.85 |
| Application Example 53 | Exemplified Compound 25 (1 pt. wt.) | Pc (A-2) (1 pt. wt.) | crystalline TiOPc (3) | 766 | 495 | 15 | 0.25 | 0.65 |
| Comparative Example 16 | Comparative Compound 2 (1 pt. wt.) | Pc (B-1) (1 pt. wt.) | crystalline TiOPc (3) | 967 | 833 | 88 | 1.27 | 7.56 |
| Comparative Example 17 | Comparative Compound 3 (1 pt. wt.) | Pc (A-2) (1 pt. wt.) | unable to be measured because dissolution in the binder solution was impossible | | | | | |
| Comparative Example 18 | Comparative Compound 4 (1 pt. wt.) | Pc (B-1) (1 pt. wt.) | crystalline TiOPc (3) | 787 | 678 | 15 | 0.85 | 2.01 |

APPLICATION EXAMPLES 54 TO 57

One part by weight of each of Exemplified Compounds 1, 2, 5, and 17 was mixed with 1 part by weight of a polycarbonate resin represented by structural formula (A-2) (POLYCARBONATE Z, manufactured by Mitsubishi Gas Chemical Company, Inc.) in 8 parts by weight of dichloroethane to dissolve the solid ingredients. Each of these solutions was applied with a doctor blade on a sheet obtained by vapor-depositing aluminum on a poly(ethylene terephthalate) (PET) film, and the coating was dried at 80° C. for 2 hours. Furthermore, a translucent gold electrode was formed on each of the thus-formed charge-transporting layers by vapor deposition to measure the carrier mobility. The measurement of carrier mobility was made by the time-of-flight method (Toshiaki Tanaka, Yasuhiro Yamaguchi, and Masaaki Yokoyama, *Denshi-Shashin*, 29, 366 (1990)) using as an illuminant a nitrogen gas laser having a pulse half width of 0.9 nsec and a wavelength of 337 nm. The results obtained at 25° C. and 25 V/µm are shown in Table 10.

COMPARATIVE EXAMPLES 19 TO 22

Sample sheets were produced in the same manner as in Application Example 54, except that each of Comparative Compound 1, Comparative Compound 5 (the same compound as that represented by formula (4)), and Comparative Compounds 6 and 7, respectively represented by the following structural formulae, was used in place of Exemplified Compound 1. These sample sheets were examined for carrier mobility. The results obtained are shown in Table 10.

Table 10 shows that the compounds of the present invention had higher carrier mobilities than the Comparative Compounds.

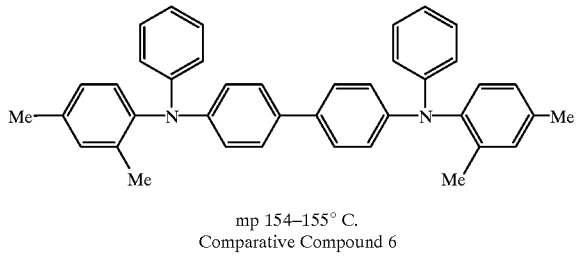

mp 154–155° C.
Comparative Compound 6

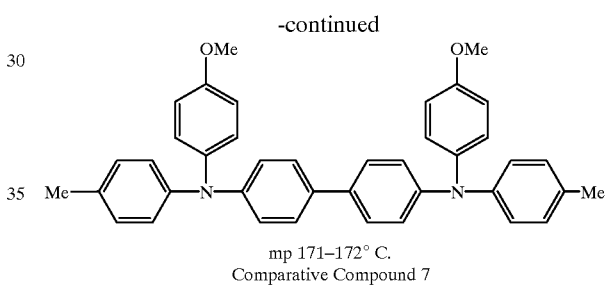

mp 171–172° C.
Comparative Compound 7

TABLE 10

| | Charge-transporting material | Carrier mobility ($cm^2V^{-1}s^{-1}$) |
|---|---|---|
| Application Example 54 | Exemplified Compound 1 | $2.24 \times 10^{-5}$ |
| Application Example 55 | Exemplified Compound 2 | $2.98 \times 10^{-5}$ |
| Application Example 56 | Exemplified Compound 5 | $2.54 \times 10^{-5}$ |
| Application Example 57 | Exemplified Compound 17 | $2.26 \times 10^{-5}$ |
| Comparative Example 19 | Comparative Compound 1 | $0.98 \times 10^{-5}$ |
| Comparative Example 20 | Comparative Compound 5 | $1.34 \times 10^{-5}$ |
| Comparative Example 21 | Comparative Compound 6 | $1.07 \times 10^{-5}$ |
| Comparative Example 22 | Comparative Compound 7 | $1.70 \times 10^{-5}$ |

APPLICATION EXAMPLES 58 AND 59

A charge-generating layer was formed in the same manner as in Application Example 1. One part by weight of each of the mixed charge-transporting materials shown in Table 11, composed of an Exemplified Compound and Comparative Compound 5 (the same compound as that represented by formula (4)), was mixed with 1 part by weight of a polycarbonate resin represented by structural formula (A-2)

(POLYCARBONATE Z-200, manufactured by Mitsubishi Gas Chemical Company, Inc.) in 8 parts by weight of dichloroethane. Each of these solutions was applied on the charge-generating layer and dried in the same manner as in Application Example 1. The photoreceptors thus obtained were examined for electrophotographic properties. The results obtained are shown in Table 11.

12, composed of an Exemplified Compound and a Comparative Compound, was mixed with 1 part by weight of a polycarbonate resin represented by structural formula (A-2) (POLYCARBONATE Z-200, manufactured by Mitsubishi Gas Chemical Company, Inc.) or a bisphenol A/biphenol type copolycarbonate resin represented by structural formula (B-1) (TOUGH Z-300, manufactured by Idemitsu

TABLE 11

|  | Charge-transporting material | Polymeric binder | Charge-generating material | $V_0$ (−V) | $V_i$ (−V) | $V_{R10}$ (−V) | $E_{1/2}$ (lx · s) | $E_{1/6}$ (lx · s) |
|---|---|---|---|---|---|---|---|---|
| Application Example 58 | Exemplified Compound 1 (0.5 pt. wt.) Comparative Compound 5 (0.5 pt. wt.) | Pc (A-2) (1 pt. wt.) | vapor-deposited TiOPc | 1046 | 805 | 4 | 0.53 | 1.25 |
| Application Example 59 | Exemplified Compound 2 (0.4 pt. wt.) Comparative Compound 5 (0.6 pt. wt.) | Pc (A-2) (1 pt. wt.) | Vapor-deposited TiOPc | 956 | 757 | 12 | 0.62 | 1.41 |

APPLICATION EXAMPLES 60 TO 64

A charge-generating layer was formed in the same manner as in Application Example 14. One part by weight of each of the mixed charge-transporting materials shown in Table 12, composed of an Exemplified Compound and a Comparative Compound, was mixed with 1 part by weight of a polycarbonate resin represented by structural formula (A-2) or (B-1). Kosan Co., Ltd.) in 8 parts by weight of dichloroethane. Each of these solutions was applied on the charge-generating layer and dried in the same manner as in Application Example 1. The photoreceptors thus obtained were examined for electrophotographic properties. The results obtained are shown in Table 12.

TABLE 12

|  | Charge-transporting material | Polymeric binder | Charge-generating material | $V_0$ (−V) | $V_i$ (−V) | $V_{R10}$ (−V) | $E_{1/2}$ (lx · s) | $E_{1/6}$ (lx · s) |
|---|---|---|---|---|---|---|---|---|
| Application Example 60 | Exemplified Compound 1 (0.5 pt. wt.) Comparative Compound 5 (0.5 pt. wt.) | Pc (A-2) (1 pt. wt.) | crystalline TiOPc (1) | 896 | 474 | 7 | 0.33 | 0.66 |
| Application Example 61 | Exemplified Compound 1 (0.5 pt. wt.) Comparative Compound 6 (0.5 pt. wt.) | Pc (B-1) (1 pt. wt.) | crystalline TiOPc (1) | 792 | 514 | 8 | 0.30 | 0.58 |
| Application Example 62 | Exemplified Compound 5 (0.5 pt. wt.) Comparative Compound 5 (0.5 pt. wt.) | Pc (A-2) (1 pt. wt.) | crystalline TiOPc (1) | 903 | 538 | 7 | 0.56 | 1.42 |
| Application Example 63 | Exemplified Compound 5 (0.5 pt. wt.) Comparative Compound 5 (0.5 pt. wt.) | Pc (B-1) (1 pt. wt.) | crystalline TiOPc (1) | 854 | 479 | 14 | 0.45 | 1.14 |
| Application Example 64 | Exemplified Compound 5 (0.5 pt. wt.) Comparative Compound 7 (0.5 pt. wt.) | Pc (B-1) (1 pt. wt.) | crystalline TiOPc (1) | 656 | 449 | 5 | 0.31 | 0.59 |

APPLICATION EXAMPLES 65 TO 67

A charge-generating layer was formed in the same manner as in Application Example 17. One part by weight of each of the mixed charge-transporting materials shown in Table 13, composed of an Exemplified Compound and either a Comparative Compound or Compound (L), represented by the following structural formula described in JP-A-1-142641, was mixed with 1 part by weight of a polycarbonate resin represented by structural formula (A-2) (POLYCARBONATE Z-200, manufactured by Mitsubishi Gas Chemical Company, Inc.) or a bisphenol A/biphenol type copolycarbonate resin represented by structural formula (B-1) (TOUGH Z-300, manufactured by Idemitsu Kosan Co., Ltd.) in 8 parts by weight of dichloroethane. Each of these solutions was applied on the charge-generating layer and dried in the same manner as in Application Example 1. The photoreceptors thus obtained were examined for electrophotographic properties. The results obtained are shown in Table 13.

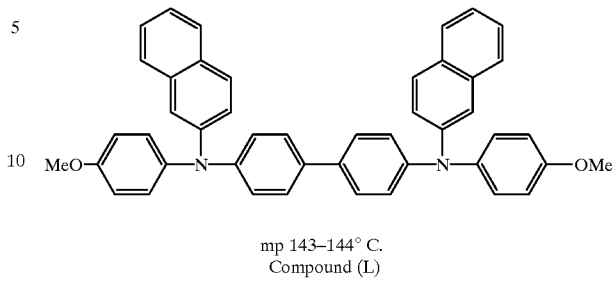

mp 143–144° C.
Compound (L)

TABLE 13

| | Charge-transporting material | Polymeric binder | Charge-generating material | $V_0$ (-V) | $V_i$ (-V) | $V_{R10}$ (-V) | $E_{½}$ (lx · s) | $E_{⅙}$ (lx · s) |
|---|---|---|---|---|---|---|---|---|
| Application Example 65 | Exemplified Compound 1 (0.5 pt. wt.) Comparative Compound 5 (0.5 pt. wt.) | Pc (A-2) (1 pt. wt.) | τ-$H_2$Pc | 745 | 645 | 10 | 0.80 | 1.43 |
| Application Example 66 | Exemplified Compound 1 (0.5 pt. wt.) Compound (L) (0.5 pt. wt.) | Pc (B-1) (1 pt. wt.) | τ-$H_2$Pc | 998 | 889 | 0 | 0.88 | 1.58 |
| Application Example 67 | Exemplified Compound 1 (0.5 pt. wt.) Comparative Compound 7 (0.5 pt. wt.) | Pc (B-1) (1 pt. wt.) | τ-$H_2$Pc | 978 | 805 | 12 | 0.71 | 1.25 |

APPLICATION EXAMPLES 68 AND 69

A charge-generating layer was formed in the same manner as in Application Example 25. One part by weight of each of the mixed charge-transporting materials shown in Table 14, composed of an Exemplified Compound and either Comparative Compound 5 (the same compound as that represented by formula (4) ) or Compound (L), was mixed with 1 part by weight of a polycarbonate resin represented by structural formula (A-2) (POLYCARBONATE Z-200, manufactured by Mitsubishi Gas Chemical Company, Inc.) or a bisphenol A/biphenol type copolycarbonate resin represented by structural formula (B-1) (TOUGH Z-300, manufactured by Idemitsu Kosan Co., Ltd.) in 8 parts by weight of dichloroethane. Each of these solutions was applied on the charge-generating layer and dried in the same manner as in Application Example 1. The photoreceptors thus obtained were examined for electrophotographic properties. The results obtained are shown in Table 14.

TABLE 14

| | Charge-transporting material | Polymeric binder | Charge-generating material | $V_0$ (-V) | $V_i$ (-V) | $V_{R10}$ (-V) | $E_{½}$ (lx · s) | $E_{⅙}$ (lx · s) |
|---|---|---|---|---|---|---|---|---|
| Application Example 68 | Exemplified Compound 1 (0.5 pt. wt.) | Pc (A-2) (1 pt. wt.) | x-$H_2$Pc | 715 | 347 | 0 | 0.55 | 1.09 |

TABLE 14-continued

| | Charge-transporting material | Polymeric binder | Charge-generating material | $V_0$ (-V) | $V_i$ (-V) | $V_{R10}$ (-V) | $E_{1/2}$ (lx·s) | $E_{1/6}$ (lx·s) |
|---|---|---|---|---|---|---|---|---|
| Application Example 69 | Compound (L) (0.5 pt. wt.) Exemplified Compound 2 (0.4 pt. wt.) Comparative compound 5 (0.6 pt. wt.) | Pc (B-1) (1 pt. wt.) | x-H₂Pc | 1088 | 999 | 11 | 1.12 | 2.21 |

APPLICATION EXAMPLE 70

A charge-generating layer was formed in the same manner as in Application Example 33. A mixed charge-transporting material composed of 0.5 part by weight of Exemplified Compound 1 and 0.5 part by weight of Comparative Compound 5 (the same compound as that represented by formula (4)) as shown in Table 15 was mixed with 1 part by weight of a polycarbonate resin represented by structural formula (A-2) (POLYCARBONATE Z-200, manufactured by Mitsubishi Gas Chemical Company, Inc.) in 8 parts by weight of dichloroethane. This solution was applied on the charge-generating layer and dried in the same manner as in Application Example 1. The photoreceptor thus obtained was examined for electrophotographic properties. The results obtained are shown in Table 15.

TABLE 15

| | Charge-transporting material | Polymeric binder | Charge-generating material | $V_0$ (-V) | $V_i$ (-V) | $V_{R10}$ (-V) | $E_{1/2}$ (lx·s) | $E_{1/6}$ (lx·s) |
|---|---|---|---|---|---|---|---|---|
| Application Example 70 | Exemplified Compound 1 (0.5 pt. wt.) Comparative compound 5 (0.5 pt. wt.) | Pc (A-2) (1 pt. wt.) | bisazo (K) | 676 | 441 | 9 | 3.80 | 6.63 |

As described above, the novel bis(3,4-methylenedioxyphenylamino) derivatives of the present invention are excellent in the performances required of charge-transporting materials. Consequently, when any of these compounds is used to produce an electrophotographic photoreceptor, it enables the photoreceptor to exhibit a high carrier mobility. In addition, since the novel compounds have good miscibility with polymer binders, the photoreceptor is satisfactory in other properties such as high sensitivity and a low residual potential. Thereafter, the compounds are industrially highly useful.

While the invention has been described in detail and with reference to specific embodiments thereof, it will be apparent to one skilled in the art that various changes and modifications can be made therein without departing from the spirit and scope thereof.

What is claimed is:

1. Bis (3,4-methylenedioxyphenylamino) derivatives represented by the following general formula (1):

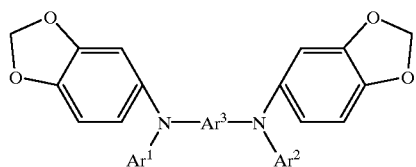

wherein $Ar^1$ and $Ar^2$ can be the same or different and each is a phenyl or naphthyl group which can be substituted with one or more lower alkyl groups having 1 to 4 carbon atoms; and $Ar^3$ represents a divalent aromatic group represented by

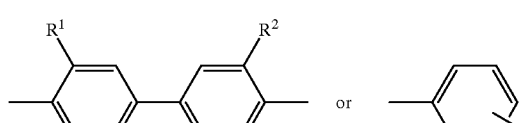

wherein $R^1$ and $R^2$ each represents a hydrogen atom, a lower alkyl group having 1 to 4 carbon atoms, or a phenyl group, provided that when $Ar^3$ is a phenylene group, one of the amino substituents is meta or para to the other.

2. An electrophotographic photoreceptor containing at least one of the bis(3,4-methylenedioxyphenylamino) derivatives of claim 1, wherein the electrophotographic receptor comprises a conductive support having thereon a photosensitive layer, which photosensitive layer comprises a charge generation material.

3. An electrophotographic photoreceptor comprising a conductive support, a charge-generating material and a charge-transporting material, wherein the charge-generating material comprises a phthalocyanine and the charge-transporting material comprises at least one of the bis(3,4-methylenedioxyphenylamino) derivatives of claim 1.

4. An electrophotographic photoreceptor comprising a conductive support, a charge-generating material and a charge-transporting material, wherein the charge-generating material comprises a phthalocyanine and the charge-transporting material comprises a combination of at least one of the bis(3,4-methylenedioxyphenylamino) derivatives of claim 1 and at least one diaminobiphenyl compound represented by the following general formula (2):

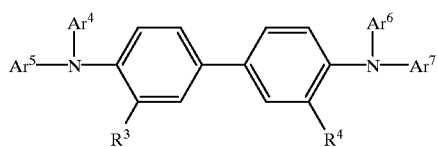
(2)

wherein $R^3$ and $R^4$ can be the same or different and each represents a hydrogen atom, a halogen atom, a lower alkyl group having 1 to 4 carbon atoms, a lower alkoxy group having 1 to 4 carbon atoms, or a phenyl group; and $Ar^4$, $Ar^5$, $Ar^6$, and $Ar^7$ can be the same or different and each represents a phenyl group which can have one or more substituents selected from the group consisting of halogen atoms, lower alkyl groups having 1 to 4 carbon atoms, and lower alkoxy groups having 1 to 4 carbon atoms or an (α-naphthyl, β-naphthyl, or biphenyl group which can have one or more substituents.

5. The electrophotographic photoreceptor of claim 4, wherein the diaminobiphenyl compounds represented by general formula (2) comprise diaminobiphenyl compounds represented by the following general formula (3):

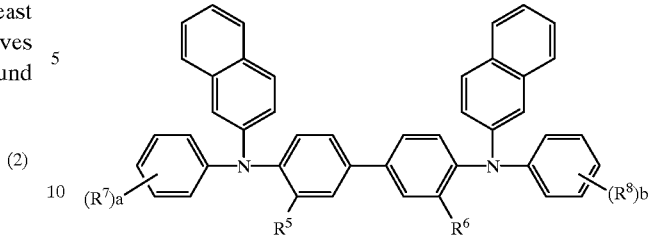
(3)

wherein $R^5$, $R^6$, $R^7$, and $R^8$ can be the same or different and each represents a hydrogen atom, a halogen atom, a lower alkyl group having 1 to 4 carbon atoms, a lower alkoxy group having 1 to 4 carbon atoms, or a phenyl group; and a and b each represents an integer of 1 or 2.

6. The electrophotographic photoreceptor of claim 4, wherein the diaminobiphenyl compound represented by general formula (2) comprise N,N'-diphenyl-N,N'-bis(3-methylphenyl)- 4,4-biphenylenediamine, represented by the following formula (4):

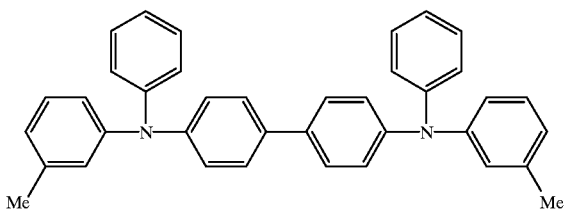
(4)

* * * * *